(12) United States Patent
Kishino et al.

(10) Patent No.: US 10,941,427 B2
(45) Date of Patent: *Mar. 9, 2021

(54) PRODUCTION SYSTEM AND METHOD OF PRODUCTION FOR PRODUCT SELECTED FROM NITROGEN-CONTAINING PRODUCT AND FERMENTED AND CULTURED PRODUCT

(71) Applicants: AJINOMOTO CO., INC., Tokyo (JP); TOKYO INSTITUTE OF TECHNOLOGY, Tokyo (JP)

(72) Inventors: Mitsuhiro Kishino, Kanagawa (JP); Hiroyuki Kojima, Kanagawa (JP); Hideo Hosono, Tokyo (JP); Michikazu Hara, Tokyo (JP); Masaaki Kitano, Tokyo (JP); Toshiharu Yokoyama, Tokyo (JP); Toru Numaguchi, Tokyo (JP); Munenobu Ito, Kanagawa (JP); Kazuteru Yamada, Kanagawa (JP); Hiromi Noguchi, Kanagawa (JP)

(73) Assignees: Ajinomoto Co., Inc., Tokyo (JP); Tokyo Institute of Technology, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/675,068

(22) Filed: Aug. 11, 2017

(65) Prior Publication Data

US 2017/0342449 A1    Nov. 30, 2017

Related U.S. Application Data

(63) Continuation of application No. PCT/CN2016/054610, filed on Feb. 17, 2016.

(30) Foreign Application Priority Data

Feb. 17, 2015 (JP) .............................. JP2015-028958

(51) Int. Cl.
*C12P 13/04* (2006.01)
*C12P 13/08* (2006.01)
(Continued)

(52) U.S. Cl.
CPC ............. *C12P 13/08* (2013.01); *B01J 21/066* (2013.01); *B01J 23/02* (2013.01); *B01J 23/462* (2013.01);
(Continued)

(58) Field of Classification Search
CPC . B01J 21/00; B01J 21/06; B01J 21/066; B01J 23/02; B01J 23/38; B01J 23/40;
(Continued)

(56) References Cited

U.S. PATENT DOCUMENTS 3,642,578 A * 2/1972 Hitzman .................. C12N 1/00
                                                    435/247
3,897,303 A * 7/1975 Sherk ........................ C01C 1/08
                                                    423/352

(Continued)

FOREIGN PATENT DOCUMENTS

CN        101006010 A     7/2007
CN        10111602 A      1/2008
(Continued)

OTHER PUBLICATIONS

Guo et al., Facile synthesis of monolithic mayenite with well-defined macropores via an epoxide-mediated sol-gel process accompanied by phase separation, Aug. 19, 2014, New J. Chem., 38, 5832-5839 (Year: 2014).*

(Continued)

*Primary Examiner* — Natasha E Young
(74) *Attorney, Agent, or Firm* — Cermak Nakajima & McGowan LLP; Shelly Guest Cermak

(57) ABSTRACT

A production system for a product selected from a nitrogen-containing product and a fermented and cultured product
(Continued)

that does not involve (or can minimize) the transport of liquid ammonia can include: an ammonia synthesis apparatus in which an ammonia-containing gas is synthesized by reaction of a source gas containing hydrogen and nitrogen in the presence of a supported metal catalyst containing as a support one or more selected from the group consisting of: i) a conductive mayenite compound; ii) a two-dimensional electride compound or a precursor thereof; and iii) a complex formed of a support base containing at least one metal oxide selected from $ZrO_2$, $TiO_2$, $CeO_2$, and MgO and a metal amide represented by a formula $M(NH_2)_x$ (where M represents one or more selected from Li, Na, K, Be, Mg, Ca, Sr, Ba, and Eu; and x represents a valence number of M) supported by the support base.

6 Claims, 5 Drawing Sheets

(51) Int. Cl.

| | |
|---|---|
| C12P 13/14 | (2006.01) |
| C12P 1/00 | (2006.01) |
| C12P 7/02 | (2006.01) |
| C12P 7/40 | (2006.01) |
| C12P 19/04 | (2006.01) |
| C12P 21/00 | (2006.01) |
| B01J 21/00 | (2006.01) |
| B01J 23/02 | (2006.01) |
| B01J 23/46 | (2006.01) |
| B01J 27/24 | (2006.01) |
| B01J 35/00 | (2006.01) |
| B01J 37/04 | (2006.01) |
| B01J 37/08 | (2006.01) |
| C07C 273/00 | (2006.01) |
| C01C 1/04 | (2006.01) |
| C01C 1/18 | (2006.01) |
| C01C 1/28 | (2006.01) |
| C01B 21/38 | (2006.01) |
| C12M 1/00 | (2006.01) |
| C12N 1/00 | (2006.01) |
| C07C 273/02 | (2006.01) |
| B01J 21/06 | (2006.01) |

(52) U.S. Cl.
CPC ........... *B01J 27/24* (2013.01); *B01J 35/0006* (2013.01); *B01J 37/04* (2013.01); *B01J 37/088* (2013.01); *C01B 21/38* (2013.01); *C01C 1/0411* (2013.01); *C01C 1/0417* (2013.01); *C01C 1/0488* (2013.01); *C01C 1/185* (2013.01); *C01C 1/28* (2013.01); *C07C 273/02* (2013.01); *C12M 1/00* (2013.01); *C12M 29/26* (2013.01); *C12N 1/00* (2013.01); *C12P 1/00* (2013.01); *C12P 7/02* (2013.01); *C12P 7/40* (2013.01); *C12P 13/04* (2013.01); *C12P 13/14* (2013.01); *C12P 19/04* (2013.01); *C12P 21/00* (2013.01); *Y02P 20/52* (2015.11)

(58) Field of Classification Search
CPC . B01J 23/46; B01J 23/462; B01J 27/00; B01J 27/24; B01J 35/00; B01J 35/0006; B01J 37/00; B01J 37/04; B01J 37/08; B01J 37/082; B01J 37/088; C01B 21/00; C01B 21/20; C01B 21/38; C01C 1/00; C01C 1/02; C01C 1/04; C01C 1/0405; C01C 1/0411; C01C 1/0417; C01C 1/0488; C01C 1/18; C01C 1/185; C01C 1/28; C07C 273/00; C07C 273/02; C12M 1/00; C12M 29/00; C12M 29/26; C12N 1/00; C12P 1/00; C12P 7/00; C12P 7/02; C12P 7/40; C12P 13/00; C12P 13/04; C12P 13/08; C12P 13/14; C12P 19/00; C12P 19/04; C12P 21/00

See application file for complete search history.

(56) References Cited

U.S. PATENT DOCUMENTS

| | | | | |
|---|---|---|---|---|
| 4,671,893 | A * | 6/1987 | Pinto | C01B 3/025 252/374 |
| 6,955,797 | B1 * | 10/2005 | Speth | C01C 1/0441 422/148 |
| 8,623,313 | B2 * | 1/2014 | Nakamura | C01B 3/042 423/352 |
| 8,987,513 | B2 * | 3/2015 | Iijima | C07C 273/04 564/67 |
| 9,150,423 | B2 | 10/2015 | Hosono et al. | |
| 9,573,822 | B2 * | 2/2017 | Hosono | C01F 7/164 |
| 10,322,940 | B2 * | 6/2019 | Hosono | C01B 21/0923 |
| 2005/0260108 | A1 | 11/2005 | Del Prato et al. | |
| 2007/0243590 | A1 | 10/2007 | Takeshita et al. | |
| 2013/0183224 | A1 | 7/2013 | Hosono et al. | |
| 2015/0239747 | A1 | 8/2015 | Hosono et al. | |
| 2016/0271595 | A1 | 9/2016 | Chen et al. | |
| 2017/0342450 | A1 * | 11/2017 | Kishino | B01J 23/58 |

FOREIGN PATENT DOCUMENTS

| | | | | |
|---|---|---|---|---|
| CN | 103237599 | A | 8/2013 | |
| CN | 103977828 | A | 8/2014 | |
| EP | 1813677 | A1 | 8/2007 | |
| EP | 2650047 | A1 | 10/2013 | |
| GB | 199032 | | 3/1924 | |
| JP | 06-114235 | A | 4/1994 | |
| JP | 11-029320 | A | 2/1999 | |
| JP | 2003-020221 | A | 1/2003 | |
| JP | 2007-307558 | A | 11/2007 | |
| JP | 2008-247654 | A | 10/2008 | |
| JP | 2011-521134 | A | 7/2011 | |
| WO | WO2006/038695 | A1 | 4/2006 | |
| WO | WO2009/142682 | A2 | 11/2009 | |
| WO | WO2012/077658 | A1 | 6/2012 | |
| WO | WO-2013088564 | A1 * | 6/2013 | ........... C07C 273/04 |
| WO | WO2014/034473 | A1 | 3/2014 | |
| WO | WO2014/129256 | A1 | 8/2014 | |

OTHER PUBLICATIONS

Kim et al., The scalable pinacol coupling reaction utilizing the inorganic electride [Ca2N]+*e* as an electron donor, 2014, Chem. Commun., 50, 4791-4794 (Year: 2014).*

Extended European Search Report for European Patent App. No. 16752519.5 (dated Aug. 23, 2018).

Appl, M., "Ammonia, 2. Production Processes," In: Ullmann's Encyclopedia of Industrial Chemistry 2012;3:139-225, Wiley-VCH Verlag GmbH & Co. KGaA, Weinheim, XP55359081A.

Kitano, M., et al., "Catalytic Ammonia Synthesis over Ruthenium-loaded 12CaO.7Al2O3 Electride," Shokubai, 2013; vol. 55, No. 4, pp. 239-245.

Kitano, M., et al., "Ammonia synthesis using a stable electride as an electron donor and reversible hydrogen store," Nature Chemistry 2012;4:934-940.

Muroi, T., "Latest Trends in Industrial Catalyst vol. 3 Ammonia Synthesis Catalyst," IC Lab Co., Ltd., Engineering materials, 2012; vol. 60, No. 10, pp. 82-86.

International Search Report and Written Opinion for PCT Patent App. No. PCT/JP2016/054610 (dated Apr. 26, 2016) with English translation of the ISR.

Office Action for Chinese Patent App. No. 201680010599.4 (dated Feb. 11, 2019) with English translation thereof.

(56) References Cited

OTHER PUBLICATIONS

Office Action from Japanese Patent App. No. 2017-500720 (dated Sep. 3, 2019) with English language translation thereof.
Office Action for Chinese Patent App. No. 201680010599.4 (dated Sep. 30, 2019) with English language translation thereof.
Final Office Action from Japanese Patent App. No. 2017-500720 (dated Mar. 24, 2020), with English language translation thereof.

* cited by examiner

PRODUCTION SYSTEM AND METHOD OF PRODUCTION FOR PRODUCT SELECTED FROM NITROGEN-CONTAINING PRODUCT AND FERMENTED AND CULTURED PRODUCT

This application is a Continuation of, and claims priority under 35 U.S.C. § 120 to, International Application No. PCT/JP2016/054610, filed Feb. 17, 2016, published as WO 2016/133133, and claims priority therethrough under 35 U.S.C. § 119 to Japanese Patent Application No. 2015-028958, filed Feb. 17, 2015, the entireties of which are incorporated by reference herein.

BACKGROUND OF THE INVENTION

Field of the Invention

The present invention relates to a production system and a method of production for nitrogen-containing products and fermented and cultured products.

Brief Description of the Related Art

Ammonia has a wide variety of uses, such as a raw material in various kinds of nitrogen-containing products, a nitrogen source in fermentation and culture, and a pH adjuster.

The Haber-Bosch process is known as an industrial large-scale production process for ammonia. In the Haber-Bosch process, a source gas containing hydrogen and nitrogen reacts under high-temperature, high-pressure conditions at 400° C. to 600° C. and 20 MPa to 100 MPa using a doubly promoted iron catalyst obtained by adding a few percent by weight of $Al_2O_3$ and $K_2O$ to $Fe_3O_4$ to synthesize ammonia.

Apart from the doubly promoted iron catalyst used in the Haber-Bosch process that is known as an ammonia synthesis catalyst, other active metal catalysts can include those with ruthenium, cobalt, osmium, rhenium, nickel, or the like. Among these, the ruthenium catalyst is known to exhibit excellent catalytic performance in ammonia synthesis under low-pressure conditions. Techniques have been disclosed in which a source gas containing hydrogen and nitrogen reacts under low pressure conditions using a supported metal catalyst in which a conductive mayenite compound supports active metals such as ruthenium to synthesize ammonia, for example (see WO 2010/077658, and Nobunaga et al., "Ammonia synthesis by $12CaO.7Al_2O_3$ electride supporting ruthenium", Shokubai, Vol. 55, No. 4, 239-245 (2013); Kitano et al., "Ammonia synthesis using a stable electride as an electron donor and reversible hydrogen store", Nature Chemistry, 2012, Vol. 4, 934-940 (2012).

Global demand for ammonia is increasing, and ammonia synthesis plants tend to upsize (See "Saishin Kogyo Shokubai Doko Dai 3-Kai Ammonia Gosei Shokubai", Kogyo Zairyo, Vol. 60, No. 10, 82-86 (2012), for example).

SUMMARY OF THE INVENTION

The synthesis of ammonia by a large-scale production process assumes that the ammonia that is produced is liquefied, and then stored and transported as liquid ammonia to ammonia consumption sites, that is, the production sites of ammonia-related products. In addition to the cost of ammonia synthesis itself, also required are costs associated with the storage and transport of liquid ammonia, and these prices tend to be high.

Although the production costs associated with ammonia synthesis can be somewhat reduced by employing an ammonia synthesis process that uses low-pressure conditions and a ruthenium catalyst instead of the Haber-Bosch process, which requires high-temperature, high-pressure conditions, there is no reduction in costs associated with the storage and transport of liquid ammonia.

Furthermore, storage and maintenance equipment for liquid ammonia are required at the ammonia consumption sites. Thus, in the production of the ammonia-related products, such as a nitrogen-containing product and a fermented and cultured product, for example, peripheral costs associated with the storage, transport, and maintenance of liquid ammonia are high.

An aspect of the present invention is to provide a novel production system and a production method for a nitrogen-containing product and a fermented and cultured product that do not involve, or can minimize, the transport and storage of liquid ammonia.

It is an aspect of the present invention to provide a production system useful for reacting a source gas and a metal catalyst to produce a product selected from the group consisting of a nitrogen-containing product and a fermented and cultured product, the production system comprising: A) an ammonia synthesis apparatus configured to react a source gas comprising hydrogen and nitrogen in the presence of a metal catalyst and a support, wherein said support is selected from the group consisting of: i) a conductive mayenite compound; ii) a two-dimensional electride compound or a precursor thereof; iii) a complex formed of a support base comprising a metal oxide selected from the group consisting of $ZrO_2$, $TiO_2$, $CeO_2$, MgO, and combinations thereof, and a metal amide represented by a formula $M(NH_2)_x$, wherein M is selected from the group consisting of Li, Na, K, Be, Mg, Ca, Sr, Ba, Eu, and combinations thereof, and x represents a valence number of M; and iv) combinations thereof; wherein an ammonia-containing gas is synthesized; and B) a production apparatus that produces said product using ammonia originating from said ammonia-containing gas.

It is a further aspect of the present invention to provide the production system as described above, wherein said ammonia synthesis apparatus is configured to react the source gas under conditions comprising a reaction temperature of 530° C. or lower and a reaction pressure of 30 MPa or lower.

It is a further aspect of the present invention to provide the production system as described above, further comprising an ammonia concentration apparatus that is configured to concentrate the ammonia from said ammonia-containing gas.

It is a further aspect of the present invention to provide the production system as described above, further comprising a recycle apparatus that is configured to recover unreacted hydrogen and nitrogen following said reaction in the ammonia synthesis apparatus and return said unreacted hydrogen and nitrogen to be reacted again in the ammonia synthesis apparatus.

It is a further aspect of the present invention to provide the production system as described above, wherein the recycle apparatus comprises a dehydrator and/or a drier configured to remove water from said unreacted hydrogen and nitrogen.

It is a further aspect of the present invention to provide the production system as described above, wherein the production system is configured to produce ammonia water using the ammonia originating from said ammonia-containing gas and produces a fermented and cultured product using said ammonia water.

It is a further aspect of the present invention to provide the production system as described above, wherein the production system is configured to produce ammonia water using the ammonia originating from said ammonia-containing gas, recovers ammonia gas from said ammonia water, and produces a fermented and cultured product using said ammonia gas.

It is a further aspect of the present invention to provide the production system as described above, wherein the nitrogen-containing product is selected from the group consisting of ammonia water, ammonium salts, urea, nitric acid, and nitrates.

It is a further aspect of the present invention to provide the production system as described above, wherein the fermented and cultured product is selected from the group consisting of amino acids, organic acids, polysaccharides, proteins, antibiotics, alcohols, and microbial cells.

It is a further aspect of the present invention to provide a method of production for a product selected from the group consisting of a nitrogen-containing product and a fermented and cultured product, the method comprising the steps of: (A) reacting a source gas comprising hydrogen and nitrogen in the presence of a metal catalyst and a support, wherein said support is selected from the group consisting of: i) a conductive mayenite compound; ii) a two-dimensional electride compound or a precursor thereof; iii) a complex formed of a support base comprising: a metal oxide selected from the group consisting of $ZrO_2$, $TiO_2$, $CeO_2$, MgO, and combinations thereof, and a metal amide represented by a formula $M(NH_2)_x$, wherein M is selected from the group consisting of Li, Na, K, Be, Mg, Ca, Sr, Ba, Eu, and combinations thereof, and x represents a valence number of M; iv) and combinations thereof; wherein an ammonia-containing gas is synthesized; and (B) producing said product using ammonia originating from said ammonia-containing gas.

It is a further aspect of the present invention to provide the method as described above, wherein step (A) and step (B) are successively performed.

It is a further aspect of the present invention to provide the method as described above, wherein the source gas is reacted under conditions comprising a reaction temperature of 530° C. or lower and a reaction pressure of 30 MPa or lower in step (A).

It is a further aspect of the present invention to provide the method as described above, further comprising concentrating ammonia within the ammonia-containing gas obtained in step (A).

It is a further aspect of the present invention to provide the method as described above, further comprising recovering unreacted hydrogen and nitrogen after step (A) and recycling said unreacted hydrogen and nitrogen to step (A).

It is a further aspect of the present invention to provide the method as described above, wherein the recycling includes performing dehydration treatment and/or drying treatment removing water from said unreacted hydrogen and nitrogen.

It is a further aspect of the present invention to provide the method as described above, wherein ammonia water is produced using ammonia originating from the ammonia-containing gas obtained in step (A) and a fermented and cultured product is produced using the obtained ammonia water in step (B).

It is a further aspect of the present invention to provide the method as described above, wherein ammonia water is produced using ammonia originating from the ammonia-containing gas obtained in step (A), ammonia gas is recovered from the obtained ammonia water, and a fermented and cultured product is produced using the recovered ammonia gas in step (B).

It is a further aspect of the present invention to provide the method as described above, wherein the nitrogen-containing product is selected from the group consisting of ammonia water, ammonium salts, urea, nitric acid, and nitrates.

It is a further aspect of the present invention to provide the method as described above, wherein the fermented and cultured product is selected from the group consisting of amino acids, organic acids, polysaccharides, proteins, antibiotics, alcohols, and microbial cells.

The present invention provides a novel production system and a method of production for a nitrogen-containing product and a fermented and cultured product.

The production system and the method of production as described herein do not involve, or can minimize, the transport of liquid ammonia and can thereby simplify and reduce the peripheral equipment and costs associated with the storage, transport, and maintenance of liquid ammonia.

DESCRIPTION OF THE EXEMPLARY EMBODIMENTS

Figure 1:
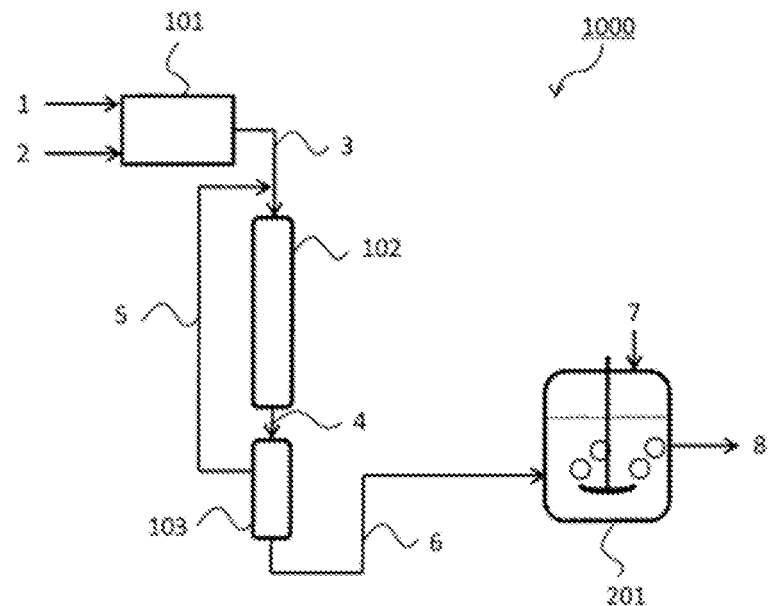
FIG. 1 is a schematic diagram (1) of a production system for ammonia water in one embodiment of the present invention.

The following describes the present invention in detail in conformity with exemplary embodiments thereof.

A novel production system is provided for producing ammonia-related products using ammonia.

As described above, ammonia synthesis by a large-scale production system assumes that synthesized ammonia is liquefied, and then stored and transported in liquid form to ammonia consumption sites, such as the production sites of ammonia-related products, and peripheral costs associated with the storage, transport and maintenance of liquid ammonia are increasing.

As described herein, ammonia is produced in an amount required for the production of ammonia-related products at the site of production of the ammonia-related products, that is, produced on site. In this way, the ammonia-related products can be produced without the storage and transport of liquid ammonia.

In one embodiment, the production system is configured to produce a nitrogen-containing product and a fermented and cultured product, wherein the system can include an ammonia synthesis apparatus, which is configured to synthesize an ammonia-containing gas by reaction of a source gas containing hydrogen and nitrogen in the presence of a supported metal catalyst containing as a support one or more of the following: i) a conductive mayenite compound; ii) a two-dimensional electride compound or a precursor thereof; and iii) a complex formed of a support base containing at least one metal oxide such as $ZrO_2$, $TiO_2$, $CeO_2$, and $MgO$, and a metal amide represented by a formula $M(NH_2)_x$, where M represents one or more of Li, Na, K, Be, Mg, Ca, Sr, Ba, and Eu; and x represents a valence number of M, supported by the support base; and a production apparatus that produces a nitrogen-containing product and a fermented and cultured product using ammonia originating from the ammonia-containing gas obtained by using the ammonia synthesis apparatus.

The "nitrogen-containing product" can refer to products containing a nitrogen atom originating from ammonia. Examples of the nitrogen-containing product can include, but are not limited to, ammonia water, ammonium salts, urea, nitric acid, and nitrates. Examples of the ammonium salts can include inorganic ammonium salts such as ammonium sulfate, ammonium nitrate, and ammonium chloride; and organic ammonium salts such as ammonium formate, ammonium acetate, ammonium citrate, and alkyl ammonium compounds. Examples of the nitrates can include potassium nitrate, sodium nitrate, and calcium nitrate.

The "fermented and cultured product" can refer to products of a fermentation and culture process when ammonia is used as a nitrogen source or a pH adjuster. Examples of the fermented and cultured products can include, but are not limited to, organic compounds such as amino acids, organic acids, polysaccharides, proteins, antibiotics, and alcohols and microbial cells.

<Ammonia Synthesis Apparatus>

In the ammonia synthesis apparatus of the production system, the ammonia-containing gas can be synthesized by reaction of the source gas containing hydrogen and nitrogen in the presence of the supported metal catalyst containing as the support one or more of: i) the conductive mayenite compound; ii) the two-dimensional electride compound or the precursor thereof; and iii) the complex formed of the support base containing at least one metal oxide such as $ZrO_2$, $TiO_2$, $CeO_2$, and $MgO$, and a metal amide represented by the formula $M(NH_2)_x$, where M represents one or more of Li, Na, K, Be, Mg, Ca, Sr, Ba, and Eu; and x represents a valence number of M, supported by the support base.

(i) Conductive Mayenite Compound

The "conductive mayenite compound" used as the support of the supported metal catalyst is a mayenite compound containing conduction electrons. The mayenite compound can refer to mayenite as a mineral itself, mayenite rocks, and complex oxides having the same crystal structure as that of a mineral mayenite crystal. The crystal of the mayenite compound is formed by basket-shaped structures (cages) with an inner diameter of about 0.4 nm that share their wall faces to be connected to each other in a three-dimensional manner. The cages of the mayenite compound normally contain negative ions such as $O^{2-}$, which can be replaced with conduction electrons by annealing. A longer annealing time increases conduction electron density within the mayenite compound.

A representative composition of the conductive mayenite compound is represented by the formula $[Ca_{24}Al_{28}O_{64}]^{4+}(O^{2-})_{2-x}(e^-)_{2x}$ ($0<x\le2$). In view of ammonia synthesis activity, the conduction electron density within the mayenite compound can be $10^{15}$ cm$^{-3}$ or higher, $10^{16}$ cm$^{-3}$ or higher, $10^{17}$ cm$^{-3}$ or higher, or $10^{18}$ cm$^{-3}$ or higher. The upper limit of the conduction electron density, which is not limited to a particular value, can be normally $2.2\times10^{21}$ cm$^{-3}$ or lower, $2.0\times10^{21}$ cm$^{-3}$ or lower, or the like. The conduction electron density within the mayenite compound can be measured by a method described in WO 2012/077658, for example.

In the conductive mayenite compound, part or all of the Ca contained in the formula of the representative composition may be replaced with one or more typical metal elements or transition metal elements, such as Li, Na, K, Mg, Sr, Ba, Sc, Ti, V, Cr, Mn, Fe, Co, Ni, Cu, Ir, Ru, Rh, and Pt. Part or all of the Al contained in the representative composition may be replaced with one or more typical metal elements or transition metal elements, such as B, Ga, C, Si, Fe, and Ge. Furthermore, part or all of the O contained in the formula of the representative composition may be replaced with one or more typical elements or transition elements, such as H, F, Cl, Br, and Au. The conductive mayenite compound can be prepared by a method described in WO 2012/077658, for example.

The conductive mayenite compound may be an electride of the conductive mayenite compound. Examples of such a conductive mayenite compound can include an electride of a mixed oxide of calcium and aluminum, that is, an electride of $12CaO\cdot7Al_2O_3$.

ii) Two-Dimensional Electride Compound or Precursor Thereof

The "two-dimensional electride compound" used as the support of the supported metal catalyst can refer to a layered compound in which electrons are present as negative ions between layers, that is, an electride in which the layers are connected via the electrons present between the layers.

In the two-dimensional electride compound, the electrons are present in spatial gaps as negative ionic electrons delocalized in a two-dimensional manner. Consequently, the electrons can move across the entire compound extremely smoothly.

In 2013, it was disclosed that $Ca_2N$ was a two-dimensional electride (see K. Lee, S. W. Kim, Y. Toda, S. Matsuishi, and H. Hosono, "Nature," 494, 336-341 (2013)). $Ca_2N$ is a layered compound in which electrons are connected as negative ions between layers formed of $[Ca_2N]^+$ and is obtained by heating $Ca_3N_2$ and metal Ca in a vacuum. It is reported that $Ca_2N$ has a conduction electron density of $1.39\times10^{22}$/cm$^3$ and a work function of 2.6 eV. After that, this two-dimensional electride was disclosed (see A. Walsh and D. O. Scanlon, Journal of Materials Chemistry C, 1, 3525-3528 (2013)). Furthermore, a nitride electride having a layered crystalline structure and formed of a nitride represented by an ion formula $[AE_2N]^+e^-$ (AE is at least one element selected from Ca, Sr, and Ba) was disclosed (see Japanese Patent Application Laid-open No. 2014-24712).

Examples of the two-dimensional electride compound that can be used as the support of the supported metal catalyst can include a nitride electride represented by a formula $M^1_2N$, where $M^1$ represents Ca, Sr, and/or Ba, and/or a carbide electride represented by a formula $M^2_2C$, where $M^2$ represents Y, Sc, Gd, Tb, Dy, Ho, and/or Er. Part of $M^1$ and $M^2$ may be substituted with one or more alkaline metal elements, such as Li, Na, K, Rb, and Cs.

A precursor of the two-dimensional electride compound may be used as the support. $Ca_3N_2$ or a hydride of calcium nitride represented by a formula CaxNyHz (1<x<11, 1<y<8, and 0<z<4) can be used as a precursor of $Ca_2N$ as the two-dimensional electride compound, for example. Examples of the hydride of calcium nitride (hereinafter, a "Ca—N—H-based compound") can include $Ca_2NH$, $CaNH$, and $Ca(NH_2)_2$. Precursors of $Sr_2N$ and $Ba_2N$ are similar to the precursor of $Ca_2N$.

Consequently, in one embodiment, the precursor of the two-dimensional electride compound can be nitrides represented by a formula $M^1_3N_2$ and/or compounds represented by a formula $M^1xNyHz$ (1<x<11, 1<y<8, and 0<z<4), where $M^1$ represents Ca, Sr, and/or Ba.

The two-dimensional electride compound may be prepared by a known method. $Ca_2N$ is obtained by mixing $Ca_3N_2$ and metal Ca and heating the mixture for a long time (about 100 hours at a high temperature of about 800° C.) under a vacuum, for example.

When the supported metal catalyst is formed by causing the two-dimensional electride compound or the precursor thereof to support metals exhibiting catalytic ability for ammonia synthesis, ammonia synthesis activity tremendously improves, and a catalyst having extremely high performance that is stable even in a long-term reaction can be achieved.

iii) Complex of Metal Oxide and Metal Amide

A complex formed of a support base containing at least one metal oxide, such as $ZrO_2$, $TiO_2$, $CeO_2$, and MgO, and a metal amide represented by a formula $M(NH_2)_x$, where M is Li, Na, K, Be, Mg, Ca, Sr, Ba, and/or Eu, supported by the support base is also suitable as the support of the supported metal catalyst.

When $Ca(NH_2)_2$ is used as the metal amide, for example, $Ca(NH_2)_2$ changes to the Ca—N—H-based compound such as $Ca_2N$, $Ca_2NH$, and CaNH in an ammonia synthesis condition and cooperates with an active metal to enhance a function as active species. With this enhancement, the supported metal catalyst containing the complex as the support can achieve stable catalytic activity for a long time in ammonia synthesis.

Active carbon, graphite, metal oxides, and the like can be used as the support base; particularly examples are support bases the surface of which exhibits basicity to neutrality such as $ZrO_2$, $TiO_2$, $CeO_2$, and MgO, or the support base may contain one or more of these. The support base can be either powdery and molded ones.

The support amount of the metal amide in the complex can be 1 wt % to 90 wt %, or 10 wt % to 40 wt %.

In view of sufficiently covering the surface of the support base with the metal amide to obtain expected catalytic activity, the complex can be prepared such that, when the specific surface area of the support base is A ($m^2/g$) and the support amount of the metal amide in the complex is B (wt %), B/A will be 0.07 wt % or more, 0.1 wt % or higher, 0.2 wt % or higher, 0.3 wt % or higher, or 0.4 wt % or higher. In view of obtaining expected catalytic activity, the upper limit of B/A can be 2.3 wt % or lower, 2.0 wt % or lower, 1.8 wt % or lower, 1.6 wt % or lower, or 1.5 wt % or lower.

The active metal of the supported metal catalyst is not limited to a particular metal so long as it is a metal exhibiting catalytic ability for ammonia synthesis through the direct reaction of hydrogen and nitrogen; examples thereof can include one or more metals belonging to the sixth group, the seventh group, the eighth group, and the ninth group of the periodic table and compounds containing the metals. Examples of the periodic table sixth group metals can include Cr, Mo, and W. Examples of the periodic table seventh group metals can include Mn, Tc, and Re. Examples of the periodic table eighth group metals can include Fe, Ru, and Os. Examples of the periodic table ninth group metals can include Co, Rh, and Ir. Examples of the compounds containing these metals can include nitrides of these metals; examples thereof can include $Co_3Mo_3N$, $Fe_3Mo_3N$, $Ni_2Mo_3N$, and $Mo_2N$.

In view of ammonia synthesis activity, the support amount of the active metal in the supported metal catalyst can be 0.01 wt % or more, 0.02 wt % or more, 0.03 wt % or more, 0.05 wt % or more, 0.1 wt % or more, 0.3 wt % or more, 0.5 wt % or more, or 1 wt % or more when the support is 100 wt %. In view of suppressing the sintering of active metal particles during an ammonia synthesis reaction to be able to retain expected ammonia synthesis activity, the upper limit of the support amount of the active metal can be 30 wt % or less, 20 wt % or less, 15 wt % or less, or 10 wt % or less.

The specific surface area of the metal catalyst, which is not limited to a particular value, can be 0.1 $m^2/g$ to 250 $m^2/g$, or 0.5 $m^2/g$ to 200 $m^2/g$. The specific surface area of the metal catalyst can be measured by a BET adsorption method, for example.

The metal catalyst can be prepared by a known method using the support and the active metal. The metal catalyst containing the conductive mayenite compound as the support can be prepared by a method described in WO 2012/077658, for example.

In the production system, the ammonia synthesis apparatus is not limited to a particular configuration so long as it is configured to react the source gas containing hydrogen and nitrogen in the presence of the catalyst to synthesize ammonia gas, and the apparatus can include an inlet for the source gas containing hydrogen and nitrogen, a reaction unit in which the source gas reacts in the presence of the catalyst to synthesize the ammonia-containing gas, and an outlet for the produced ammonia-containing gas, for example.

In the reaction unit of the ammonia synthesis apparatus, hydrogen and nitrogen in the source gas directly react in accordance with a formula: $3H_2+N_2 \leftrightarrows 2NH_3$ under the effect of the catalyst to synthesize ammonia.

In view of making ammonia synthesis at the ammonia consumption sites easy, the reaction temperature can be 600° C. or lower, or 550° C. or lower. The supported metal catalyst containing the support of above-specified i) to iii) can achieve excellent ammonia synthesis activity even when the reaction temperature is further lowered. The reaction temperature may be 530° C. or lower, 500° C. or lower, 450° C. or lower, or 400° C. or lower, for example. In view of ammonia synthesis activity, the lower limit of the reaction temperature can be 100° C. or higher, 150° C. or higher, 200° C. or higher, 250° C. or higher, or 300° C. or higher. In the reaction unit of the ammonia synthesis apparatus, the temperature may be uniform, or a temperature gradient may be provided so as to give different temperatures between a reaction unit inlet and a reaction unit outlet.

In view of making ammonia synthesis at the ammonia consumption sites easy, the reaction pressure can be 30 MPa or lower, 25 MPa or lower, or 20 MPa or lower. The supported metal catalyst containing the support of above-specified i) to iii) can achieve excellent ammonia synthesis activity even when the reaction pressure is further lowered. The reaction pressure may be 15 MPa or lower, 10 MPa or lower, 5 MPa or lower, 4 MPa or lower, 3 MPa or lower, 2 MPa or lower, or 1 MPa or lower, for example. In view of the ammonia concentration at the outlet of the ammonia synthesis apparatus governed by chemical equilibrium in one preferred embodiment, the lower limit of the reaction pressure can be 10 kPa or higher, 50 kPa or higher, or 100 kPa or higher. The reaction pressure is a gauge pressure (the same applies to the following).

In the reaction unit of the ammonia synthesis apparatus, the reaction mode may be any of a batch reaction mode, a closed circulatory system reaction mode, and a flow system reaction mode; in view of practicality, the flow system reaction mode is preferred. Known reactor structures can be employed such as an internal heat exchange type for the purpose of retaining an ammonia synthesis reaction rate at a high level by controlling an increase in the temperature of a catalyst layer by reaction and increasing equilibrium ammonia concentration, and a quencher type that supplies the source gas in a divided manner in a fluid flow direction.

In the reaction unit of the ammonia synthesis apparatus, one supported metal catalyst may be used alone, or two or more supported metal catalysts may be used in combination. When two or more supported metal catalysts are used, in accordance with a reaction mode, the two or more supported metal catalysts may be used after mixing with each other, the supported metal catalysts may be used by stacking them so as to form separate layers by type, or the supported metal catalysts may be filled into separate reaction tubes so as to be filled into different reaction tubes by type and then used by combining the reaction tubes.

When using the supported metal catalyst containing the support of above-specified i) to iii), in obtaining expected ammonia synthesis activity, it is important to reduce the water content within the source gas. In view of the stability of the catalyst in particular, the water content within the source gas can be 100 ppm by volume or lower, or 50 ppm by volume or lower. The lower limit of the water content can be lower and may even be 0 ppm by volume. When the production system includes a recycle apparatus for unreacted hydrogen and nitrogen described below, it is important that the water content within the source gas is within the range including a water content within gas recovered by the recycle apparatus.

The molar ratio (hydrogen/nitrogen) between hydrogen and nitrogen within the source gas can be 1/1 to 10/1, or 1/1 to 5/1. When using the supported metal catalyst containing the support of the above-specified i) to iii), the influence of hydrogen poisoning can be reduced, and favorable ammonia synthesis activity can be achieved across such a wide range of molar ratios.

Hydrogen within the source gas used for ammonia synthesis can be prepared by commonly known methods such as 1) a method that transforms a hydrocarbon, such as coal, petroleum, natural gas, or biomass, for example, into gas containing CO and $H_2$ by a steam reforming reaction, a partial oxidation reaction, or a combination of these reactions and then performs a CO shift reaction and decarbonation processing, 2) a method that electrolyzes water, and 3) a method that decomposes water using a photocatalyst. Alternatively, hydrogen may be supplied from a hydrogen cylinder, including a hydrogen cylinder curdle, the same applies to the following, or a hydrogen tank, including a mobile tank such as a hydrogen self-loader, the same applies to the following. Nitrogen within the source gas used for ammonia synthesis may be prepared by separating nitrogen from air using a nitrogen separation membrane or a cryogenic separation method. Alternatively, when hydrogen is prepared utilizing the partial oxidation reaction of the hydrocarbon, nitrogen within air used as an oxygen source may be utilized. Alternatively, nitrogen may be supplied from a nitrogen cylinder, including a nitrogen cylinder curdle, the same applies to the following, or a nitrogen tank, including a mobile tank such as a nitrogen self-loader, the same applies to the following. The molar ratio (hydrogen/nitrogen) between hydrogen and nitrogen within the source gas used for ammonia synthesis essentially changes its value depending on the preparation process of hydrogen and nitrogen. When using the supported metal catalyst containing the support of the above-specified i) to iii), the influence of hydrogen poisoning can be reduced, and there is no need to adjust the molar ratio (hydrogen/nitrogen) between hydrogen and nitrogen within the source gas to be a low value through a separation operation or the like before adding to the ammonia synthesis apparatus. Consequently, the source gas containing hydrogen and nitrogen can be adjusted using a process that can be performed advantageously at the ammonia consumption sites, and additional equipment for adjusting the molar ratio (hydrogen/nitrogen) between hydrogen and nitrogen within the source gas can be omitted or simplified.

The production system may further include a source gas production apparatus that produces the source gas containing hydrogen and nitrogen. As described above, a known apparatus may be used for the source gas production apparatus. Alternatively, the production system may further include a hydrogen cylinder and/or a hydrogen tank for supplying hydrogen and may further include a nitrogen cylinder and/or a nitrogen tank for supplying nitrogen.

In the production system, the ammonia concentration within the ammonia-containing gas synthesized by the ammonia synthesis apparatus can be 0.5% by volume or higher, 2% by volume or higher, 4% by volume or higher, 6% by volume or higher, 8% by volume or higher, or 10% by volume or higher. The ammonia-containing gas synthesized by the ammonia synthesis apparatus mainly contains unreacted hydrogen and unreacted nitrogen apart from ammonia.

In the production system, the ammonia synthesis capacity (ammonia-ton/day) of the ammonia synthesis apparatus, which varies by the amount of ammonia usage in the production apparatus for the ammonia-related products, can be 300 ton/day or less, 200 ton/day or less, 100 ton/day or less, 80 ton/day or less, 60 ton/day or less, or 50 ton/day or less. The lower limit of the ammonia synthesis capacity, which is not limited to a particular amount, can be normally 0.1 ton/day or more, 1 ton/day or more, 2 ton/day or more, or the like.

<Product Production Apparatus>

In the production system as described herein, a product production apparatus can produce a nitrogen-containing product and a fermented and cultured product using ammonia originating from the ammonia-containing gas obtained by using the ammonia synthesis apparatus.

The nitrogen-containing product and the fermented and cultured product are as described above. Ammonia is extremely important as the source of nitrogen as an essential nutrient for use in fermentation or the pH adjuster. In conventional techniques that synthesize ammonia by the large-scale production process, the production sites of these ammonia-related products are typically geographically remote from the ammonia synthesis sites, and ammonia produced at the ammonia synthesis sites must be transported as liquid ammonia to the production sites of the ammonia-related products. At the production sites of the ammonia-related products, the transported liquid ammonia is stored and is used as it is or after being converted into an appropriate use mode such as ammonia water or ammonia gas in accordance with the production process of the ammonia-related products.

In the production system as described herein, the ammonia-related products are produced using ammonia originating from the ammonia-containing gas obtained by using the ammonia synthesis apparatus. The production system is characterized by not involving, or by minimizing, the storage and transport of liquid ammonia in the production of the ammonia-related products. In accordance with the specific specification of the product production apparatus, the ammonia-containing gas obtained by using the ammonia synthesis apparatus may be 1) supplied to the product production apparatus as it is, 2) supplied to the product production apparatus after being cooled, 3) supplied to the product production apparatus as concentrated ammonia gas or liquid ammonia, or ammonia water as needed, after being concentrated, or 4) supplied to a fermentation and culture apparatus by recovering ammonia gas from the obtained ammonia water and using the recovered ammonia gas.

To also include 2) to 4) as described above, the production system uses ammonia that is "originating from" the ammonia-containing gas obtained by using the ammonia synthesis apparatus.

Consequently, in one embodiment, the production system further can include a cooler that cools the ammonia-containing gas obtained by using the ammonia synthesis apparatus. The cooler is not limited to a particular cooler so long as it can cool the ammonia-containing gas to a certain temperature; any of known coolers, a coil type heat exchanger or a shell-and-tube type heat exchanger, for example, may be used. The cooled ammonia-containing gas may be supplied to the product production apparatus as it is or supplied to the product production apparatus after being stored in a storage tank.

In another embodiment, the production system further can include an ammonia concentration apparatus that concentrates the ammonia within the ammonia-containing gas obtained by using the ammonia synthesis apparatus. The ammonia concentration apparatus is not limited to a particular apparatus so long as it can concentrate the ammonia within the ammonia-containing gas; any of known concentration apparatuses may be used. Examples of the ammonia concentration apparatus can include a pressurized cooling apparatus, a gas separation membrane apparatus, and a pressure swing adsorption (PSA) apparatus.

When the pressurized cooling apparatus is used as the ammonia concentration apparatus, the conditions of pressurized cooling are suitably set so as to liquefy the ammonia within the ammonia-containing gas. Pressure during the pressurized cooling, which varies by reaction pressure in the reaction unit of the ammonia synthesis apparatus and temperature during the pressurized cooling, can be 10 kPa or higher, 50 kPa or higher, 100 kPa or higher, 0.2 MPa or higher, 0.3 MPa or higher, 0.4 MPa or higher, or 0.5 MPa or higher. The temperature during the pressurized cooling, which varies by the pressure during the pressurized cooling, can be 50° C. or lower, 40° C. or lower, 30° C. or lower, 20° C. or lower, 10° C. or lower, 5° C. or lower, 0° C. or lower, −5° C. or lower, or −10° C. or lower. The lower limit of the temperature, which is not limited to a particular temperature, can be normally −35° C. or higher, −30° C. or higher, or the like. The pressurized cooling apparatus is not limited to a particular apparatus so long as it can perform pressurized cooling of the ammonia-containing gas obtained by using the ammonia synthesis apparatus on the conditions; any of known pressurized cooling apparatuses may be used. Liquid ammonia obtained by pressurized cooling of the ammonia-containing gas may be supplied to the product production apparatus as it is or supplied to the product production apparatus after being stored in a storage tank.

When the gas separation membrane apparatus is used as the ammonia concentration apparatus, a hydrogen gas separation membrane, a nitrogen gas separation membrane, or a combination of these membranes can be suitably used. The ammonia-containing gas obtained by using the ammonia synthesis apparatus mainly contains ammonia, unreacted hydrogen, and unreacted nitrogen, and at least either the unreacted hydrogen or the unreacted nitrogen is separated by the gas separation membrane, whereby the ammonia can be concentrated. The hydrogen gas separation membrane and the nitrogen gas separation membrane are not limited to particular membranes so long as they can separate the unreacted hydrogen or nitrogen within the ammonia-containing gas obtained by using the ammonia synthesis apparatus; any of known hydrogen gas separation membranes and nitrogen gas separation membranes may be used. Alternatively, an ammonia gas separation membrane that can selectively separate the ammonia within the ammonia-containing gas may be used. In concentrating ammonia using the gas separation membrane apparatus, conditions including temperature and pressure may be determined in accordance with the type of the gas separation membrane. Pressure (on a crude gas side) during gas separation can be 10 kPa or higher, 50 kPa or higher, 100 kPa or higher, 0.2 MPa or higher, 0.3 MPa or higher, 0.4 MPa or higher, or 0.5 MPa or higher, for example. The upper limit of the gas pressure (on the crude gas side), which is not limited to a particular pressure, is normally the reaction pressure in the reaction unit of the ammonia synthesis apparatus or lower. The concentrated ammonia gas obtained by the gas separation membrane apparatus may be supplied to the product production apparatus as it is or supplied to the product production apparatus after being stored in a storage tank.

The pressure swing adsorption (PSA) apparatus may be used as the ammonia concentration apparatus. The PSA apparatus uses an adsorbent exhibiting selective adsorbability for the ammonia within the ammonia-containing gas and controls the adsorption and desorption of the ammonia by pressure change to separate the ammonia from the other gases and to concentrate the ammonia. The PSA apparatus is not limited to a particular apparatus so long as it can concentrate the ammonia within the ammonia-containing gas; any of known PSA apparatuses may be used. The ammonia within the ammonia-containing gas may be concentrated using a PSA apparatus described in Japanese Patent No. 2634015, for example. In the PSA apparatus, pressure ($P_{ad}$) when the ammonia is adsorbed to the adsorbent and pressure ($P_{de}$) when the ammonia is desorbed from the adsorbent can satisfy $P_{ad} > P_{de}$. In view of efficiently concentrating the ammonia within the ammonia-containing gas, $P_{ad}$ and $P_{de}$ can satisfy $P_{ad} - P_{de} \geq 10$ kPa, $P_{ad} - P_{de} \geq 50$ kPa, $P_{ad} - P_{de} \geq 100$ kPa, $P_{ad} - P_{de} \geq 0.2$ MPa, $P_{ad} - P_{de} \geq 0.3$ MPa, $P_{ad} - P_{de} \geq 0.4$ MPa, or $P_{ad} - P_{de} \geq 0.5$ MPa. The upper limit of the difference ($P_{ad} - P_{de}$) between $P_{ad}$ and $P_{de}$ is normally the reaction pressure in the reaction unit of the ammonia synthesis apparatus or lower. $P_{ad}$, which is not limited to a particular pressure so long as it satisfies $P_{ad} > P_{de}$, may be determined in accordance with the adsorbability of the adsorbent used and is normally the reaction pressure in the reaction unit of the ammonia synthesis apparatus or less. $P_{de}$, which is not limited to a particular pressure so long as it satisfies $P_{ad} > P_{de}$, may be determined in accordance with the adsorbability of the adsorbent used and is normally 1

MPa or lower and 0.5 MPa or lower, 0.2 MPa or lower, 100 kPa or lower, 50 kPa or lower, 10 kPa or lower, or 0 kPa or lower. Temperature during the gas separation may be determined in accordance with the specific specification of the PSA apparatus.

When the PSA apparatus is used as the ammonia concentration apparatus, the PSA apparatus suitably includes two or more adsorption towers. The PSA apparatus including two adsorption towers, a first adsorption tower and a second adsorption tower, for example, is operated so as to perform an ammonia desorption process in the second adsorption tower when an ammonia adsorption process is performed in the first adsorption tower and perform the ammonia adsorption process in the second adsorption tower when the ammonia desorption process is performed in the first adsorption tower, whereby the ammonia within the ammonia-containing gas can be continuously concentrated. The concentrated ammonia gas obtained by the PSA apparatus may be supplied to the product production apparatus as it is or supplied to the product production apparatus after being stored in a storage tank.

When the PSA apparatus is used as the ammonia concentration apparatus, ammonia concentration within the concentrated ammonia gas obtained by the ammonia concentration apparatus can be 10% by volume or higher, 30% by volume or higher, 50% by volume or higher, or 90% by volume or higher. The upper limit of the ammonia concentration can be higher and may be 100% by volume. Consequently, the "concentrating" of ammonia is a concept including the isolation of the ammonia from the ammonia-containing gas.

The ammonia-containing gas obtained by using the ammonia synthesis apparatus may be further purified using an ammonia purification apparatus after the ammonia is concentrated by the ammonia concentration apparatus.

As described above, the ammonia-containing gas obtained by using the ammonia synthesis apparatus contains the unreacted hydrogen and the unreacted nitrogen. These unreacted hydrogen and nitrogen are recycled as sources of ammonia synthesis, whereby system efficiency can be improved. Consequently, in one embodiment, the production system further can include a recycle apparatus that recovers the unreacted hydrogen and nitrogen on the downstream side of the ammonia synthesis apparatus and recycles a recovered gas to the upstream side of the ammonia synthesis apparatus.

In the embodiment in which the ammonia-containing gas obtained by using the ammonia synthesis apparatus is supplied to the product production apparatus as it is and the embodiment in which the ammonia-containing gas is supplied to the product production apparatus after being cooled, for example, it is difficult to selectively recover the unreacted hydrogen and nitrogen on the upstream side of the product production apparatus, and the recycle apparatus may be provided in the product production apparatus or on the downstream side of the product production apparatus. The details of the recycle apparatus in these embodiments will be described below with reference to the drawings.

In the embodiment in which the ammonia-containing gas obtained by using the ammonia synthesis apparatus is concentrated and supplied as the concentrated ammonia gas or liquid ammonia, or ammonia water as needed, to the product production apparatus, for example, the unreacted hydrogen and nitrogen can be selectively recovered in the ammonia concentration apparatus, and the recycle apparatus may be provided in the ammonia concentration apparatus.

The recycle apparatus is not limited to a particular apparatus so long as it can recover the unreacted hydrogen and nitrogen and recycle the recovered gas containing hydrogen and nitrogen to the upstream side of the ammonia synthesis apparatus; any of known recycle apparatuses may be used. The recycle apparatus may include a pipe for the recovered gas and a pump for transporting the recovered gas, for example.

When the recovered gas contains water, if the gas is recycled as it is, the catalytic ability of the supported metal catalyst used in the ammonia synthesis apparatus may be affected. Consequently, in one embodiment, the recycle apparatus can include a dehydrator that removes the water within the recovered gas. The dehydrator is not limited to a particular dehydrator so long as it can reduce a water content within the recovered gas to a value that does not affect the catalytic ability of the chosen supported metal catalyst; any of known dehydrators may be used. Examples of the dehydrator can include an apparatus that cools the recovered gas to condense and remove the water. In view of further reducing the water content within the recovered gas, the recycle apparatus may use a drier and may include the drier in addition to the dehydrator or in place of the dehydrator. The drier is not limited to a particular drier so long as it has a function of further reducing the water content within the recovered gas; any of known driers may be used. Examples of the drier can include an apparatus that brings the recovered gas into contact with a moisture absorbent to perform dehydration; examples of the moisture absorbent in this apparatus can include, but are not limited to, chemical moisture absorbents such as calcium chloride, diphosphorus pentaoxide, and copper sulfate anhydride; and physical moisture absorbents such as silica gel, alumina gel, and zeolite.

In the production system, the product production apparatus is configured to produce the nitrogen-containing product and the fermented and cultured product using ammonia. A basic configuration of such a product production apparatus may be similar to those of product production apparatuses known in the subject field.

The following describes embodiments of the production system including an ammonia water production apparatus, a urea production apparatus, or a fermented and cultured product production apparatus as the product production apparatus with reference to the drawings.

Production System for Ammonia Water

In the production system including the ammonia water production apparatus as the product production apparatus, ammonia water is produced using the ammonia originating from the ammonia-containing gas obtained by using the ammonia synthesis apparatus.

Figure 2:
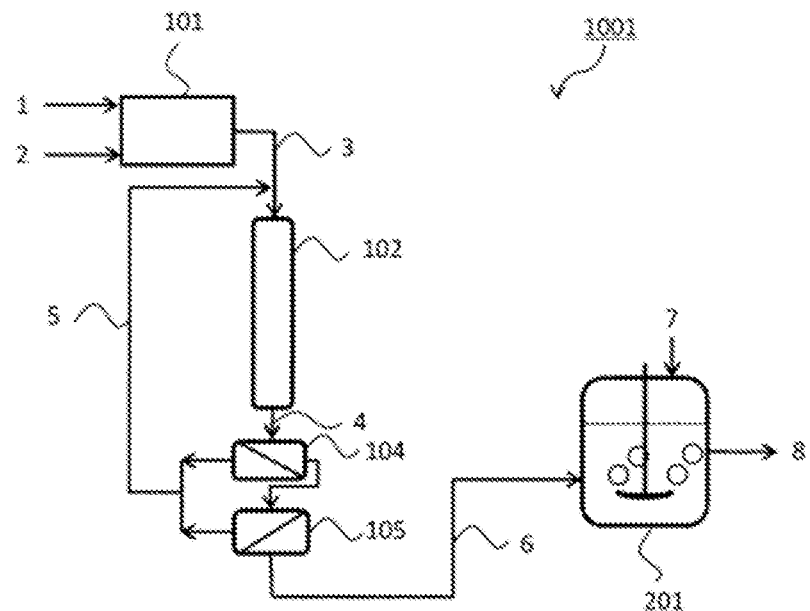
FIG. 2 is a schematic diagram (2) of a production system for ammonia water in one embodiment of the present invention.
Figure 3:
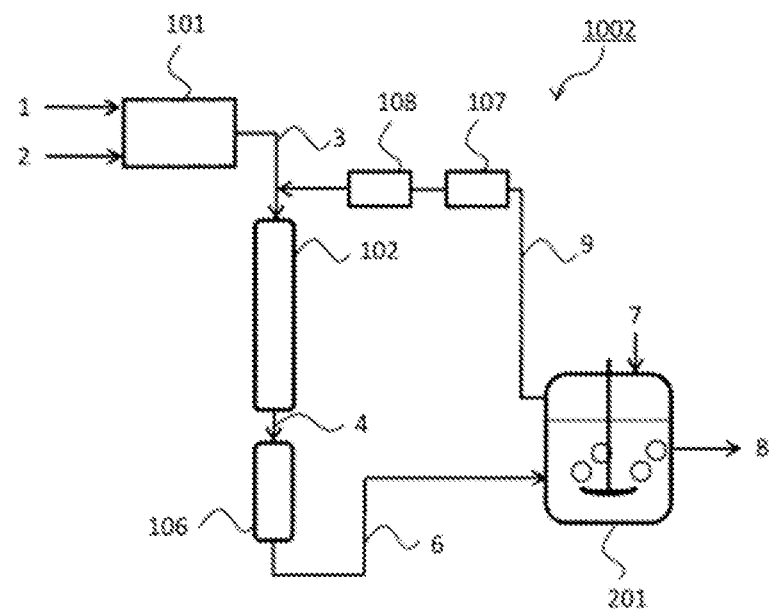
FIG. 3 is a schematic diagram (3) of a production system for ammonia water in one embodiment of the present invention.

The ammonia water production apparatus is not limited to a particular apparatus so long as it can produce ammonia water using ammonia; any of known apparatuses may be used. FIG. 1 to FIG. 3 illustrate embodiments in which a dissolving tank is used as the ammonia water production apparatus.

FIG. 1 illustrates a production system 1000 for ammonia water including a source gas production apparatus 101, an ammonia synthesis apparatus 102, an ammonia concentration apparatus 103, which can be a pressurized cooling apparatus or a PSA apparatus, and an ammonia water production apparatus 201.

In the production system 1000, first, a hydrogen source gas 1 and air 2 are supplied to the source gas production apparatus 101. The hydrogen source gas 1 may be a hydrocarbon (coal, petroleum, natural gas, or biomass, for example) or water in accordance with a hydrogen production process in the source gas production apparatus 101.

Examples of the hydrogen production process can include, as described above, 1) a method that transforms a hydrocarbon into gas containing CO and $H_2$ by a steam reforming reaction, a partial oxidation reaction, or a combination of these reactions and then performs a CO shift reaction and decarbonation processing, 2) a method that electrolyzes water, and 3) a method that decomposes water using a photocatalyst. The source gas production apparatus 101 also produces nitrogen. Nitrogen may be prepared by separating nitrogen from air using a nitrogen separation membrane or a cryogenic separation method. Alternatively, when hydrogen is prepared utilizing the partial oxidation reaction of the hydrocarbon, nitrogen within air used as an oxygen source may be used.

A source gas 3 containing hydrogen and nitrogen produced by the source gas production apparatus 101 is supplied to the ammonia synthesis apparatus 102. In the ammonia synthesis apparatus 102, the ammonia-containing gas is synthesized by reaction of the source gas containing hydrogen and nitrogen in the presence of the supported metal catalyst containing the support of above-specified i) to iii).

A synthesized ammonia-containing gas 4 is supplied to the ammonia concentration apparatus 103, which can be a pressurized cooling apparatus or a PSA apparatus. When the ammonia concentration apparatus 103 is a pressurized cooling apparatus, liquid ammonia 6 is obtained. When the ammonia concentration apparatus 103 is a PSA apparatus, concentrated ammonia gas 6 is obtained. The obtained liquid ammonia or concentrated ammonia gas may be stored in a storage tank (not illustrated).

The obtained liquid ammonia or the concentrated ammonia gas 6 is supplied to the ammonia water production apparatus 201. Water 7 is also supplied to the ammonia water production apparatus 201. The ammonia water production apparatus dissolves the liquid ammonia or the concentrated ammonia gas 6 in the water 7 and can thereby produce ammonia water 8. The method and conditions of dissolution are not limited to particular ones so long as they can produce ammonia water with expected concentration; any of known methods and conditions may be used.

The production system 1000 illustrated in FIG. 1 includes a recycle apparatus (not illustrated) that recovers unreacted hydrogen and nitrogen separated by the ammonia concentration apparatus 103 and recycles a recovered gas 5 to the upstream side of the ammonia synthesis apparatus 102.

FIG. 2 illustrates a production system 1001 for ammonia water including the source gas production apparatus 101, the ammonia synthesis apparatus 102, gas separation membrane apparatuses (ammonia concentration apparatuses) 104 and 105, and the ammonia water production apparatus 201. In the production system 1001, the source gas production apparatus 101, the ammonia synthesis apparatus 102, and the ammonia water production apparatus 201 are as described in the production system 1000.

The production system 1001 includes the gas separation membrane apparatuses 104 and 105 as the ammonia concentration apparatus. A hydrogen gas separation membrane 104 and a nitrogen gas separation membrane 105 can be used in combination, for example. The production system 1001 including the gas separation membrane apparatuses 104 and 105 can obtain the concentrated ammonia gas 6. The obtained concentrated ammonia gas may be stored in a storage tank (not illustrated).

The production system 1001 illustrated in FIG. 2 includes a recycle apparatus that recovers unreacted hydrogen and nitrogen separated by the gas separation membrane apparatuses 104 and 105 and recycles the recovered gas 5 to the upstream side of the ammonia synthesis apparatus 102.

FIG. 3 illustrates a production system 1002 for ammonia water including the source gas production apparatus 101, the ammonia synthesis apparatus 102, a cooler 106, and the ammonia water production apparatus 201. In the production system 1002, the source gas production apparatus 101, the ammonia synthesis apparatus 102, and the ammonia water production apparatus 201 are as described in the production system 1000.

In the production system 1002, the ammonia-containing gas 4 obtained by using the ammonia synthesis apparatus 102 is cooled by the cooler 106. Next, the cooled ammonia-containing gas 6 is supplied to the ammonia water production apparatus 201.

The cooled ammonia-containing gas 6 contains unreacted hydrogen and nitrogen. The production system 1002 includes a recycle apparatus that recovers the unreacted hydrogen and nitrogen in the ammonia water production apparatus 201 and recycles a recovered gas 9 to the upstream side of the ammonia synthesis apparatus 102. The recovered gas 9 contains water originating from the water 7 used in the ammonia water production apparatus 201. In the production system 1002, the recycle apparatus includes a dehydrator 107 that removes the water within the recovered gas 9. The production system 1002 also includes a drier 108 that further dries the recovered gas 9.

The production system for ammonia water has been described with reference to FIG. 1 to FIG. 3; in the production system, ammonium salts can be produced by using an inorganic acid, an organic acid, or a solution thereof in place of the water 7. The production systems illustrated in FIG. 1 to FIG. 3 include the source gas production apparatus 101; a hydrogen supply apparatus such as a hydrogen cylinder or a hydrogen tank and a nitrogen supply apparatus such as a nitrogen cylinder or a nitrogen tank may be included in place of the source gas production apparatus 101. The ammonia water obtained by the ammonia water production apparatus 201 may be subjected to concentrating the ammonia water by a concentration apparatus not illustrated. The method of concentration is performed by a known unit such as heating.

Production System for Urea

In the production system including the urea production apparatus as the product production apparatus, urea is produced using the ammonia originating from the ammonia-containing gas obtained by using the ammonia synthesis apparatus.

Figure 4:
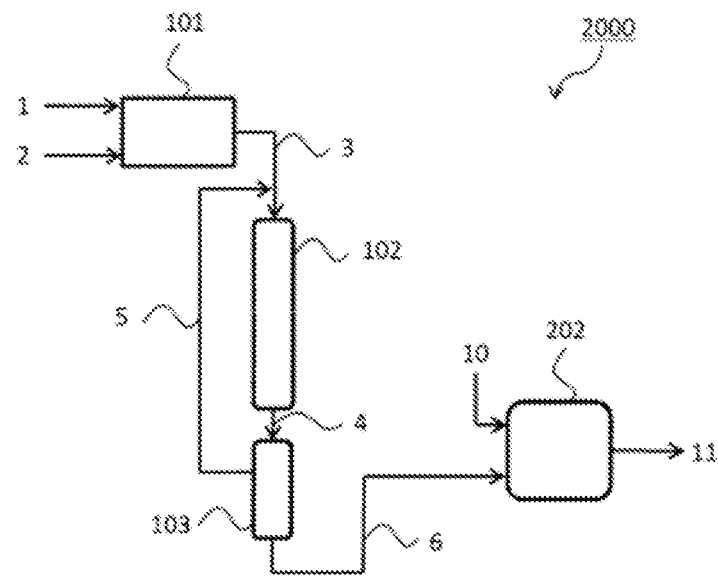
FIG. 4 is a schematic diagram (1) of a production system for urea in one embodiment of the present invention.
Figure 5:
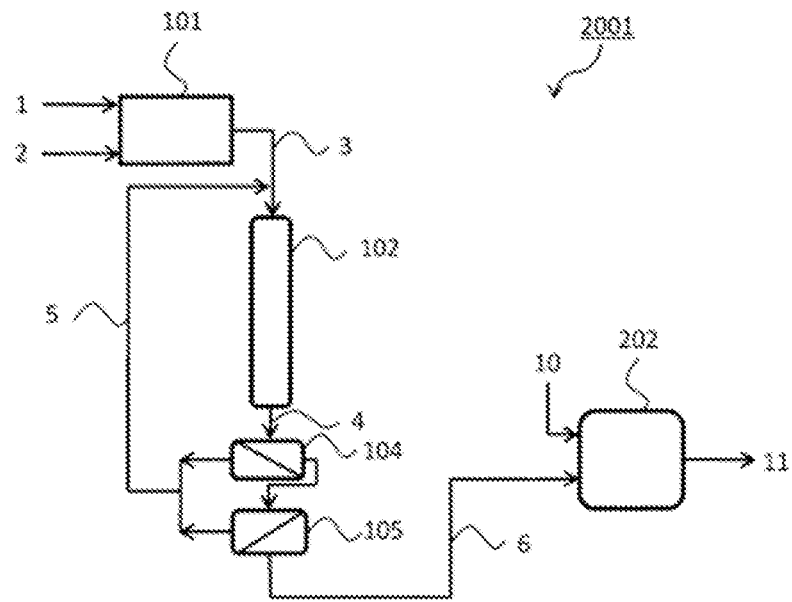
FIG. 5 is a schematic diagram (2) of a production system for urea in one embodiment of the present invention.
Figure 6:
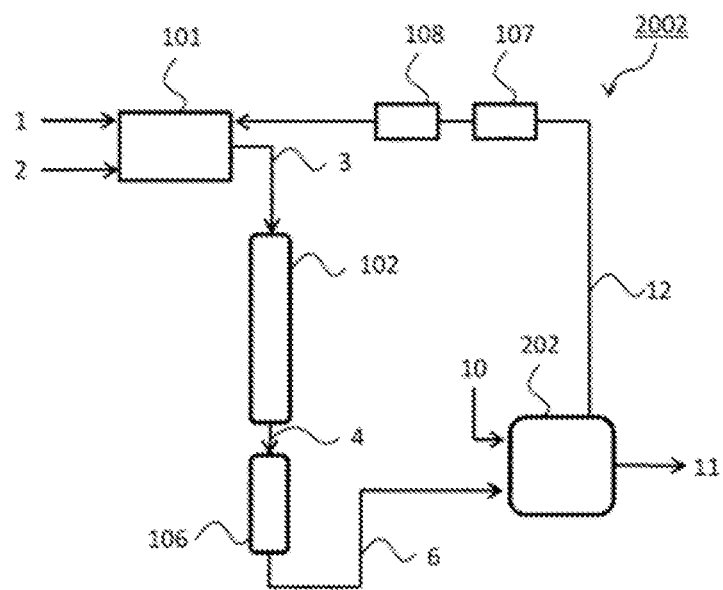
FIG. 6 is a schematic diagram (3) of a production system for urea in one embodiment of the present invention.

Urea can be produced by performing reaction of ammonia and carbon dioxide in accordance with a formula: $2NH_3 + CO_2 \rightarrow CO(NH_2)_2 + H_2O$. Also in the production system, the urea production apparatus that produces urea from ammonia and carbon dioxide is suitably used. FIG. 4 to FIG. 6 illustrate embodiments using such a urea production apparatus.

FIG. 4 illustrates a production system 2000 for urea including the source gas production apparatus 101, the ammonia synthesis apparatus 102, the ammonia concentration apparatus 103, which can be the pressurized cooling apparatus or the PSA apparatus, and a urea production apparatus 202. In the production system 2000, the source gas production apparatus 101, the ammonia synthesis apparatus 102, and the ammonia concentration apparatus 103 (pressurized cooling apparatus or PSA apparatus) are as described in the production system 1000.

In the production system 2000, the liquid ammonia or the concentrated ammonia gas 6 obtained by the ammonia concentration apparatus 103 may be supplied to the urea production apparatus 202 as is, or may be supplied to the urea production apparatus 202 after being stored in a storage tank (not illustrated). Carbon dioxide 10 is also supplied to the urea production apparatus 202. When hydrogen is produced by the steam reforming reaction of a hydrocarbon or the like in the source gas production apparatus 101, carbon dioxide in off-gas produced during the reaction may be used. The urea production apparatus 202 can produce urea 11 by performing reaction of ammonia and carbon dioxide in accordance with the formula.

The conditions of the urea production reaction are not limited to particular conditions so long as urea can be produced from ammonia and carbon dioxide in accordance with the formula; the reaction can be generally performed under conditions including 14 MPa to 25 MPa and 170° C. to 210° C. (Japanese Patent Application Laid-open No. H08-325222, for example).

The production system 2000 illustrated in FIG. 4 includes a recycle apparatus that recovers hydrogen and nitrogen separated by the ammonia concentration apparatus 103 and recycles the recovered gas 5 to the upstream side of the ammonia synthesis apparatus 102.

FIG. 5 illustrates a production system 2001 for urea including the source gas production apparatus 101, the ammonia synthesis apparatus 102, the gas separation membrane apparatuses (the ammonia concentration apparatuses) 104 and 105, and the urea production apparatus 202. In the production system 2001, the source gas production apparatus 101, the ammonia synthesis apparatus 102, the gas separation membrane apparatuses (the ammonia concentration apparatuses) 104 and 105, and the urea production apparatus 202 are as described above. The production system 2001 includes a recycle apparatus that recovers unreacted hydrogen and nitrogen separated by the gas separation membrane apparatuses 104 and 105 and recycles the recovered gas 5 to the upstream side of the ammonia synthesis apparatus 102.

In the production system 2001, the concentrated ammonia gas obtained by the gas separation membrane apparatuses 104 and 105 may be supplied to the urea production apparatus 202 as it is or supplied to the urea production apparatus 202 after being stored in a storage tank (not illustrated).

FIG. 6 illustrates a production system 2002 for urea including the source gas production apparatus 101, the ammonia synthesis apparatus 102, the cooler 106, and the urea production apparatus 202. In the production system 2002, the source gas production apparatus 101, the ammonia synthesis apparatus 102, the cooler 106, and the urea production apparatus 202 are as described above.

In the production system 2002, the ammonia-containing gas 4 obtained by using the ammonia synthesis apparatus 102 is cooled by the cooler 106. Next, the cooled ammonia-containing gas 6 is supplied to the urea production apparatus 202.

The cooled ammonia-containing gas 6 contains unreacted hydrogen and nitrogen. The production system 2002 includes a recycle apparatus that recovers the unreacted hydrogen and nitrogen in the urea production apparatus 202 and recycles a recovered gas 12 to a decarbonation unit (the upstream side of the ammonia synthesis apparatus 102) of the source gas production apparatus 101. The recovered gas 12 contains water originating from the urea production reaction. In the production system 2002, the recycle apparatus includes the dehydrator 107 that removes the water within the recovered gas 12. The production system 2002 also includes the drier 108 that further dries the recovered gas 12.

The production system for urea has been described with reference to FIG. 4 to FIG. 6; in the production systems, nitric acid can be produced by Ostwald process in the presence of an appropriate catalyst using water in place of the carbon dioxide 10. The obtained nitric acid may be further reacted to produce nitrates (potassium nitrate and sodium nitrate, for example). The production systems illustrated in FIG. 4 to FIG. 6 include the source gas production apparatus 101; a hydrogen supply apparatus such as a hydrogen cylinder or a hydrogen tank and a nitrogen supply apparatus such as a nitrogen cylinder or a nitrogen tank may be included in place of the source gas production apparatus 101.

Production System for Fermented and Cultured Product

In the production system including the fermented and cultured product production apparatus as the product production apparatus, a fermented and cultured product is produced using the ammonia originating from the ammonia-containing gas obtained by using the ammonia synthesis apparatus.

Examples of the fermented and cultured product can include organic compounds such as amino acids, organic acids, polysaccharides, proteins, antibiotics, and alcohols and microbial cells. Examples of the amino acids can include glycine, alanine, valine, leucine, isoleucine, serine, threonine, cysteine, cystine, methionine, phenylalanine, tyrosine, tryptophan, proline, hydroxyproline, asparagine, glutamine, aspartic acid, glutamic acid, lysine, histidine, and arginine. Examples of the organic acids can include acetic acid, lactic acid, pyruvic acid, succinic acid, malic acid, itaconic acid, citric acid, acrylic acid, propionic acid, and fumaric acid. Examples of the polysaccharides can include xanthan, dextran, alginate, hyaluronic acid, curdlan, gellan, scleroglucan, and pullulan. Examples of the proteins can include hormones, lymphokines, interferons, and enzymes, such as amylase, glucoamylase, invertase, lactase, protease, and lipase. Examples of the antibiotics can include antimicrobial agents, such as β-lactams, macrolides, ansamycin, tetracycline, chloramphenicol, peptidergic antibiotics, and aminoglycosides, antifungal agents, such as polyoxin B, griseofulvin, and polyenemacrolides, anticancer agents, such as daunomycin, adriamycin, dactinomycin, mithramycin, and bleomycin, protease/peptidase inhibitors, such as leupeptin, antipain, and pepstatin, and cholesterol biosynthesis inhibitors, such as compactin, lovastatin, and pravastatin. Examples of the alcohols can include ethanol, isopropanol, glycerin, propylene glycol, trimethylene glycol, 1-butanol, and sorbitol. Other examples of the fermented and cultured product can include organic compounds such as acrylamide, diene compounds, such as isoprene, and pentanediamine. Techniques that culture microorganisms having organic compound productivity to produce the above organic compounds are widely known. The methods as described herein can be applied widely to such microorganism fermentation techniques. In microorganism fermentation, microorganisms themselves grow utilizing a carbon source, a nitrogen source, or the like. In that sense, the fermented and cultured product can include microbial cells. Examples of the microbial cells can include any microorganisms having organic compound productivity.

The microorganisms having organic compound productivity can include both 1) microorganisms intrinsically having organic compound productivity and 2) microorganisms that have acquired organic compound productivity through the introduction of organic compound production genes by gene recombination, although they do not have or do not substantially have organic compound productivity intrinsically. As to the microorganisms having organic compound productivity, various kinds of microorganisms are known in accordance with the type of organic compounds; these known microorganisms may be widely used. So long as ammonia can be used as the nitrogen source or the pH adjuster in culture, the methods as described herein can be widely applied also to microorganisms to be developed in the future.

The microorganisms, which are not limited to particular microorganisms so long as they have organic compound productivity, can be bacteria or fungi. Examples of the bacteria can include the *Escherichia* bacteria, the *Pantoea* bacteria, the *Corynebacterium* bacteria, the *Enterobacter* bacteria, the *Clostridium* bacteria, the *Bacillus* bacteria, the *Lactobacillus* bacteria, the *Streptomyces* bacteria, the *Streptococcus* bacteria, and the *Pseudomonas* bacteria. Examples of the fungi can include the *Saccharomyces* fungi, the *Schizosaccharomyces* fungi, the *Yarrowia* fungi, the *Trichoderma* fungi, the *Aspergillus* fungi, the *Fusarium* fungi, and the *Mucor* fungi.

Examples of the *Escherichia* bacteria can include *Escherichia coli*. Examples of the *Pantoea* bacteria can include *Pantoea ananatis*. Examples of the *Corynebacterium* bacteria can include *Corynebacterium glutamicum* and *Corynebacterium ammoniagenes*. Examples of the *Enterobacter* bacteria can include *Enterobacter aerogenes*. Examples of the *Clostridium* bacteria can include *Clostridium acetobutylicum*. Examples of the *Bacillus* bacteria can include *Bacillus subtilis* and *Bacillus amyloliquefaciens*. Examples of the *Lactobacillus* bacteria can include *Lactobacillus yamanashiensis, Lactobacillus animalis, Lactobacillus hilgardii*, and *Lactobacillus brevis*. Examples of the *Streptomyces* bacteria can include *Streptomyces clavuligerus, Streptomyces venezuelae*, and *Streptomyces peucetius*. Examples of *Streptococcus* bacteria can include *Streptococcus equi* and *Streptococcus mutans*. Examples of the *Pseudomonas* bacteria can include *Pseudomonas fluorescens, Pseudomonas aeruginosa, Pseudomonas elodea*, and *Pseudomonas putida*. Examples of the *Saccharomyces* fungi can include *Saccharomyces cerevisiae*. Examples of the *Schizosaccharomyces* fungi can include *Schizosaccharomyces pombe*. Examples of the *Yarrowia* fungi can include *Yarrowia lipolytica*. Examples of the *Trichoderma* fungi can include *Trichoderma reesei*. Examples of the *Aspergillus* fungi can include *Aspergullus terreus* and *Aspergillus oryzae*. Examples of the *Fusarium* fungi can include *Fusarium hetereosporum*. Examples of the *Mucor* fungi can include *Mucor javanicus*.

When the production system produces amino acids, examples of the microorganisms that can be suitably used can include the following: when the target substance is L-lysine, for example, examples thereof can include *Escherichia Coli* A J11442 (NRRL B-12185, FERM BP-1543) (refer to U.S. Pat. No. 4,346,170), *Brevibacterium lactofermentum* AJ3990 (ATCC31269) (refer to U.S. Pat. No. 4,066,501), and Lys-producing bacteria WC196LC/pCABD2 (WO 2010/061890). WC196ΔcadAΔldc is a strain constructed by destroying the cadA and ldcC genes that code lysine decarboxylase from the WC196 strain. WC196ΔcadAΔldc/pCABD2 is a strain constructed by introducing a plasmid pCABD2 (U.S. Pat. No. 6,040,160) containing a lysine biosynthetic gene to WC196ΔcadAΔldc. WC196ΔcadAΔldc was named AJ110692 and was deposited at International Patent Organism Depositary, National Institute of Advanced Industrial Science and Technology (currently Patent Microorganisms Depositary, National Institute of Technology and Evaluation, No. 120, 2-5-8 Kazusaka-matari, Kisarazu-shi, Chiba 292-0818, Japan) with an accession number of FERM BP-11027 on Oct. 7, 2008. Examples thereof for L-threonine can include *Escherichia Coli* VKPM B-3996 (MA 1867, VKPM B-3996) (refer to U.S. Pat. No. 5,175,107) and *Corynebacterium acetoacidophilum* AJ12318 (FERM BP-1172) (refer to U.S. Pat. No. 5,188,949); examples thereof for L-phenylalanine can include *Escherichia Coli* AJ12604 (FERM BP-3579) (refer to European Patent Application Laid-open No. 488,424), and *Brevibacterium lactofermentum* AJ12637 (FERM BP-4160) (refer to French Patent Application Laid-open No. 2,686,898); examples thereof for L-glutamic acid can include *Escherichia Coli* AJ12624 (FERM BP-3853) (refer to French Patent Application Laid-open No. 2,680,178) and *Brevibacterium lactofermentum* AJ12475 (FERM BP-2922) (refer to U.S. Pat. No. 5,272,067), and 225641dhAΔsucAyggB* prepared with *Corynebacterium glutamicum* ATCC13869 as a mother strain (WO 2014/185430); examples thereof for L-leucine can include *Escherichia Coli* AJ11478 (FERM P-5274) (refer to Japanese Examined Patent Application Publication No. S62-34397) and *Brevibacterium lactofermentum* AJ3718 (FERM P-2516) (refer to U.S. Pat. No. 3,970,519); examples thereof for L-isoleucine can include *Escherichia Coli* KX141 (VKPM B-4781) (refer to European Patent Application Laid-open No. 519,113) and *Brevibacterium flavum* AJ12149 (FERM BP-759) (refer to U.S. Pat. No. 4,656,135); and examples thereof for L-valine can include *Escherichia Coli* VL1970 (VKPM B-4411) (refer to European Patent Application Laid-open No. 519,113) and *Brevibacterium lactofermentum* AJ12341 (FERM BP-1763) (refer to U.S. Pat. No. 5,188,948).

When the production system produces organic acids, examples of the microorganisms that can be suitably used can include the following: when the target substance is L-lactic acid, for example, examples thereof can include *Lactobacillus yamanashiensis, Lactobacillus animalis*, and *Saccharomyces cerevisiae*; examples thereof for pyruvic acid can include *Escherichia Coli* and *Pseudomonas fluorescens*; examples thereof for succinic acid can include *Escherichia Coli* and *Pantoea ananatis*; examples thereof for itaconic acid can include *Aspergillus terreus*; and examples thereof for citric acid can include *Escherichia Coli* (refer to WO 2007/097260 and Japanese Patent Application Laid-open No. 2010-187542, for example).

When the production system produces polysaccharides, examples of the microorganisms that can be suitably used can include the following: when the target substance is dextran, for example, examples thereof can include *Lactobacillus hilgardii* and *Streptococcus mutans*; examples thereof for alginate can include *Pseudomonas aeruginosa*; examples thereof for hyaluronic acid can include *Streptococcus equi* and *Streptococcus mutans*; and examples thereof for gellan can include *Pseudomonas elodea* (refer to Japanese Patent Application Laid-open No. 2011-116825 and Japanese Patent Application Laid-open No. 2007-9092, for example).

When the production system produces proteins, examples of the microorganisms that can be suitably used can include the following: when the target substance is any of various kinds of hormones or interferons, for example, examples thereof can include *Saccharomyces cerevisiae*; examples thereof for amylase, glucoamylase, protease, or lipase can include *Bacillus subtilis* and *Aspergillus oryzae*; and examples thereof for invertase or lactase can include *Saccharomyces cerevisiae* and *Aspergillus oryzae* (refer to WO 2006/67511 and Japanese Patent Application Laid-open No. 2003-153696, for example).

When the production system produces antibiotics, examples of the microorganisms that can be suitably used can include the following: when the target substance is a β-lactam such as penicillin, for example, examples thereof can include *Pseudomonas putida* and *Streptomyces clavuligerus*; examples thereof for macrolides such as erythromycin and azithromycin can include *Streptomyces venezuelae*; examples thereof for daunomycin can include *Streptomyces peucetius*; examples thereof for pravastatin can include *Streptomyces clavuligerus* (refer to WO 96/10084, Japanese Patent Application Laid-open No. 2002-53589, WO 2005/54265, and WO 2007/147827, for example).

When the production system produces alcohols, examples of the microorganisms that can be suitably used can include the following: when the target substance is ethanol, for example, examples thereof can include *Saccharomyces cerevisiae, Schizosaccharomyces pombe*, and *Lactobacillus brevis*; and examples thereof for trimethylene glycol can include *Escherichia coli* (refer to WO 2007/97260, for example).

The fermented and cultured product production apparatus is not limited to a particular apparatus so long as it can produce the fermented and cultured product using ammonia as the nitrogen source or the pH adjuster; any known apparatuses may be used depending on the type of the fermented and cultured product. FIG. 7 to FIG. 10 illustrate embodiments using a fermentation and culture tank.

Figure 7:
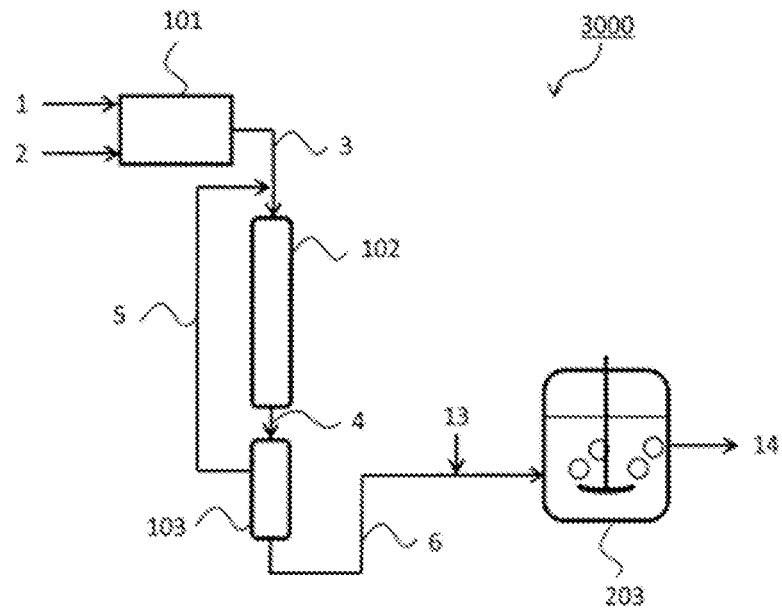
FIG. 7 is a schematic diagram (1) of a production system for a fermented and cultured product in one embodiment of the present invention.

FIG. 7 illustrates a production system 3000 for a fermented and cultured product including the source gas production apparatus 101, the ammonia synthesis apparatus 102, the ammonia concentration apparatus 103, which can be the pressurized cooling apparatus or the PSA apparatus, and a fermented and cultured product production apparatus 203. In the production system 3000, the source gas production apparatus 101, the ammonia synthesis apparatus 102, and the ammonia concentration apparatus 103 (the pressurized cooling apparatus or the PSA apparatus) are as described in the production system 1000.

In the production system 3000, the liquid ammonia or the concentrated ammonia gas 6 obtained by the ammonia concentration apparatus 103 may be directly supplied to the fermented and cultured product production apparatus 203, or may be supplied to the fermented and cultured product production apparatus 203 after being stored in a storage tank (not illustrated). An appropriate fermentation and culture medium liquid in accordance with the type of the fermentation and culture product to be produced is introduced to the fermented and cultured product production apparatus 203, and air 13 is supplied thereto as needed to perform fermentation and culture using the ammonia 6 as the nitrogen source or the pH adjuster, whereby a fermented and cultured product 14 can be produced.

Fermentation and culture conditions are not limited to particular conditions so long as the conditions can produce the fermented and cultured product to be produced; any of standard fermentation and culture conditions may be used. The fermentation and culture temperature is normally 20° C. to 37° C. In accordance with the characteristics of the microorganism used, fermentation and culture may be performed under an aerobic, anoxic, or anaerobic condition. As to the method of fermentation and culture, known methods such as a batch method, a fed-batch method, and a continuous method may be used.

The production system 3000 illustrated in FIG. 7 includes a recycle apparatus that recovers unreacted hydrogen and nitrogen separated by the ammonia concentration apparatus 103 and recycles the recovered gas 5 to the upstream side of the ammonia synthesis apparatus 102.

Figure 8:
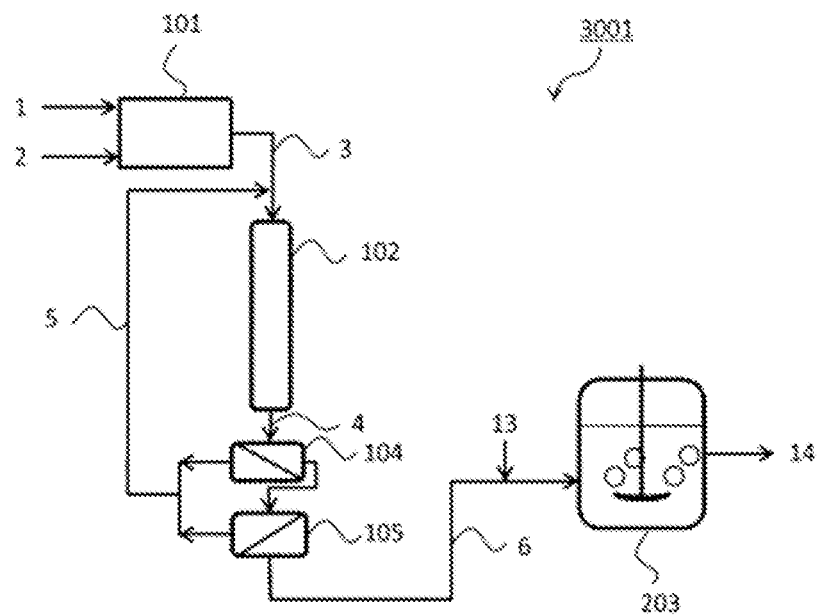
FIG. 8 is a schematic diagram (2) of a production system for a fermented and cultured product in one embodiment of the present invention.

FIG. 8 illustrates a production system 3001 for a fermented and cultured product including the source gas production apparatus 101, the ammonia synthesis apparatus 102, the gas separation membrane apparatuses (the ammonia concentration apparatuses) 104 and 105, and the fermented and cultured product production apparatus 203. In the production system 3001, the source gas production apparatus 101, the ammonia synthesis apparatus 102, the gas separation membrane apparatuses (the ammonia concentration apparatuses) 104 and 105, and the fermented and cultured product production apparatus 203 are as described above. The production system 3001 includes a recycle apparatus that recovers unreacted hydrogen and nitrogen separated by the gas separation membrane apparatuses 104 and 105 and recycles the recovered gas 5 to the upstream side of the ammonia synthesis apparatus 102.

In the production system 3001, the concentrated ammonia gas obtained by the gas separation membrane apparatuses 104 and 105 may be supplied to the fermented and cultured product production apparatus 203 as is, or may be supplied to the fermented and cultured product production apparatus 203 after being stored in a storage tank (not illustrated).

Figure 9:
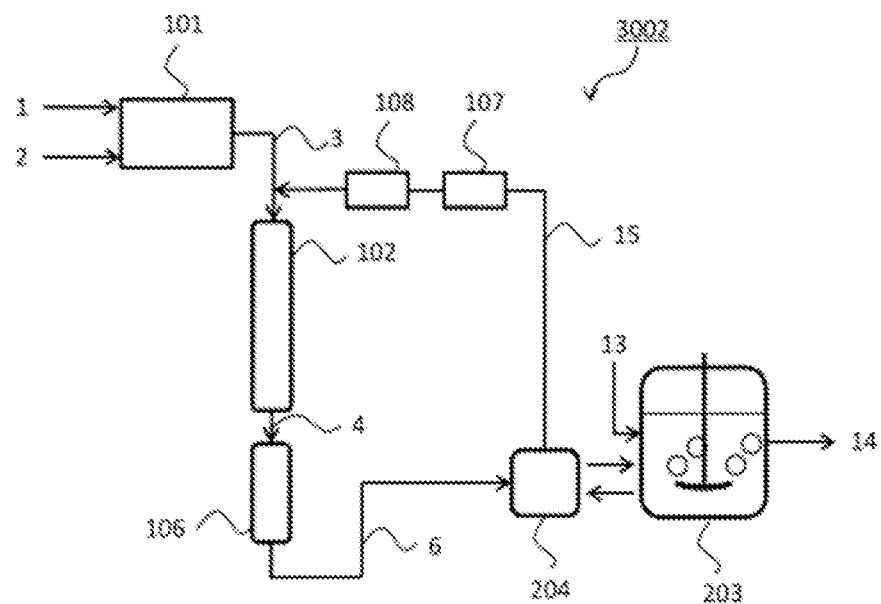
FIG. 9 is a schematic diagram (3) of a production system for a fermented and cultured product in one embodiment of the present invention.

FIG. 9 illustrates a production system 3002 for a fermented and cultured product including the source gas production apparatus 101, the ammonia synthesis apparatus 102, the cooler 106, and the fermented and cultured product production apparatus 203. In the production system 3002, the source gas production apparatus 101, the ammonia synthesis apparatus 102, and the cooler 106 are as described above.

In the production system 3002, the fermented and cultured product production apparatus 203 includes a premixer 204. Between the premixer 204 and the fermentation and culture tank of the fermented and cultured product production apparatus 203, the fermentation and culture medium liquid circulates. In the premixer 204, ammonia is premixed with the circulating fermentation and culture medium liquid. With this premixing, the fermentation and culture medium liquid mixed with ammonia is supplied to the fermentation and culture tank of the fermented and cultured product production apparatus 203.

In the production system 3002, the ammonia-containing gas 4 obtained by using the ammonia synthesis apparatus 102 is cooled by the cooler 106. Next, the cooled ammonia-containing gas 6 is supplied to the premixer 204.

The cooled ammonia-containing gas 6 contains unreacted hydrogen and nitrogen. The production system 3002 includes a recycle apparatus that recovers the unreacted hydrogen and nitrogen in the premixer 204 and recycles a recovered gas 15 to the upstream side of the ammonia synthesis apparatus 102. The recovered gas 15 contains water originating from the fermentation and culture medium liquid. In the production system 3002, the recycle apparatus includes the dehydrator 107 that removes the water within the recovered gas 15. The production system 3002 also includes the drier 108 that further dries the recovered gas 15.

Figure 10:
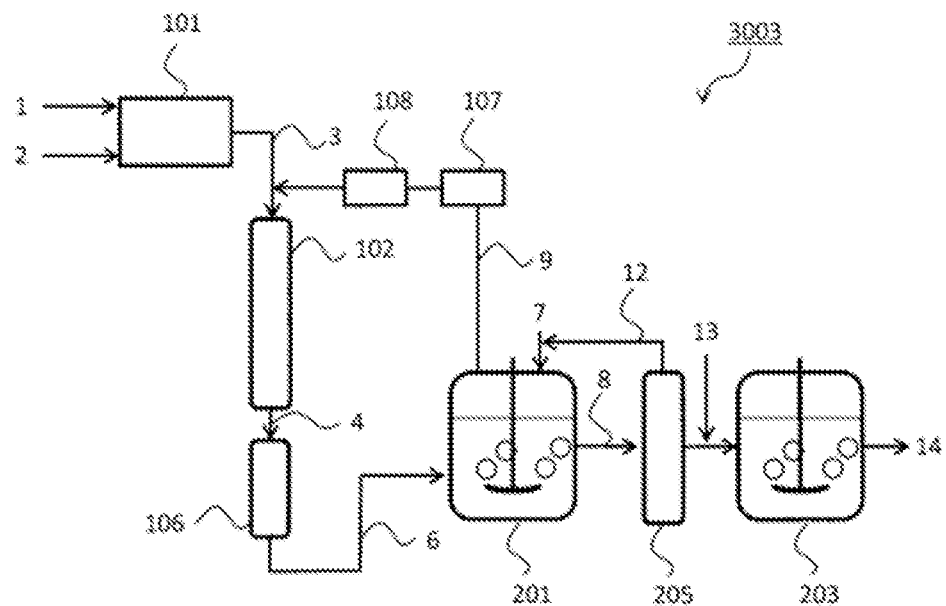
FIG. 10 is a schematic diagram (4) of a production system for a fermented and cultured product in one embodiment of the present invention.

FIG. 10 illustrates a production system 3003 for a fermented and cultured product including the source gas production apparatus 101, the ammonia synthesis apparatus 102, the cooler 106, the ammonia water production apparatus 201, an ammonia stripping apparatus 205, and the fermented and cultured product production apparatus 203. In the production system 3003, the source gas production apparatus 101, the ammonia synthesis apparatus 102, the cooler 106, and the ammonia water production apparatus 201 are as described above.

The production system 3003 is a modification of the production system 1002. In the production system 3003, the produced ammonia water 8 is used further for the production of the fermented and cultured product. Specifically, the produced ammonia water 8 is supplied to the ammonia stripping apparatus 205 to recover ammonia gas from the ammonia water. The ammonia stripping apparatus 205 is not limited to a particular apparatus so long as it can recover the ammonia gas from the ammonia water; any of known stripping apparatuses may be used. The ammonia gas recovered by the ammonia stripping apparatus 205 is supplied as the nitrogen source or the pH adjuster to the fermented and cultured product production apparatus 203 to perform fermentation and culture, whereby the fermented and cultured product 14 can be produced.

Water 12 removed by the ammonia stripping apparatus 205 may be merged with the water 7 as illustrated in FIG. 10 or discharged.

The production system 3003 can also transport the ammonia water 8 produced by the ammonia water production apparatus 201 and produce the fermented and cultured product at geographically remote sites. Although the production system 3003 is a production system for a fermented and cultured product, the fermented and cultured product production apparatus 203 may be replaced with a production apparatus for other nitrogen-containing products such as urea, nitric acid, and nitrates. Such a modification is also included in the production system described herein.

The production systems for a fermented and cultured product have been described with reference to FIG. 7 to FIG. 10; in the production systems, a hydrogen supply apparatus, such as a hydrogen cylinder or a hydrogen tank, and a nitrogen supply apparatus, such as a nitrogen cylinder or a nitrogen tank, may be used in place of the source gas production apparatus 101. In the production systems for a fermented and cultured product illustrated in FIG. 7 to FIG. 9, the concentrated ammonia 6, such as the liquid ammonia or the concentrated ammonia gas, is also suitably supplied to the fermented and cultured product production apparatus 203 after being converted into ammonia water.

The nitrogen-containing product produced by the production system can be suitably used as raw materials of various kinds of chemical products and fertilizers. The fermented and cultured product produced by the production system can be suitably used for foods, drugs, chemical reagents, and the like.

Method of Production

The systems and methods described herein also provide a novel method of production for the ammonia-related products. The method of production does not involve, or minimizes, the transport of liquid ammonia.

In one embodiment, the method of production is for a a nitrogen-containing product and/or a fermented and cultured product, the method including:

(A) performing reaction of a source gas containing hydrogen and nitrogen in the presence of a supported metal catalyst containing as a support one or more of: i) a conductive mayenite compound; ii) a two-dimensional electride compound or a precursor thereof; and iii) a complex formed of a support base containing at least one metal oxide, such as $ZrO_2$, $TiO_2$, $CeO_2$, and $MgO$, and a metal amide represented by a formula $M(NH_2)_x$, where M represents one or more of Li, Na, K, Be, Mg, Ca, Sr, Ba, and Eu; and x represents a valence number of M, supported by the support base to synthesize an ammonia-containing gas; and (B) producing a nitrogen-containing product and/or a fermented and cultured product using ammonia originating from the obtained ammonia-containing gas.

The supported metal catalyst, the source gas, the ammonia-containing gas used in Process (A) and conditions (temperature, pressure, and the like) when the ammonia-containing gas is synthesized are as described in the section herein entitled "Production System". The nitrogen-containing product and the fermented and cultured product produced in Process (B) and the method of production for the same are as described in the section herein entitled "Production System". The advantageous effects described for the production system are also applied to the method of production similarly.

In the method of production, Process (A) and Process (B) are successively performed. The phrase "Process (A) and Process (B) are successively performed" can mean that the ammonia-containing gas synthesized in Process (A) is subjected to Process (B) without being transported as liquid ammonia. The phrase "Being transported as liquid ammonia" can mean transport between two geographically remote sites by pipeline, air, ship, automobile, and the like and does not include transport within a production site of the ammonia-related products.

The method of production may further include a process of producing the source gas containing hydrogen and nitrogen from the hydrogen source gas and air. The methods of production for the hydrogen source gas and the source gas are as described in the section herein entitled "Production System".

The method of production may further include a process of concentrating the ammonia within the ammonia-containing gas obtained in Process (A). The method for concentrating the ammonia within the ammonia-containing gas is as described in the section herein entitled "Production System".

The method of production may further include a process (hereinafter, referred to as Process (C)) of recovering unreacted hydrogen and nitrogen and recycling a recovered gas to Process (A). In one embodiment, Process (C) may include dehydration treatment and/or drying treatment removing water within the recovered gas. The methods of dehydration treatment and the drying treatment are as described in the section herein entitled "Production System".

One preferred embodiment of the method of production produces ammonia water using the ammonia originating from the ammonia-containing gas obtained in Process (A) and produces a fermented and cultured product using the obtained ammonia water in Process (B).

Another preferred embodiment of the method of production produces ammonia water using the ammonia originating from the ammonia-containing gas obtained in Process (A), recovers ammonia gas from the obtained ammonia water, and produces a fermented and cultured product using the recovered ammonia gas in Process (B).

When the fermented and cultured product is produced, the method of production may further include collecting a metabolite from a medium liquid after the end of fermentation and culture. The method for collecting the metabolite is not limited to a particular method; the metabolite can be collected by combining an ion exchange resin method, a precipitation method, and other methods that have been conventionally commonly known.

EXAMPLES

Reference Example 1

<Synthesis of $Ca_3N_2$ Supporting Ru>

In a glove box in an Ar atmosphere, 1 g of commercially available $Ca_3N_2$ powder was physically mixed with $Ru_3(CO)_{12}$ and was encapsulated in vacuum quartz glass. The glass-encapsulated sample was heated at 250° C. for 15 hours. With this procedure, a $Ca_3N_2$ catalyst supporting 2 wt % Ru metal was obtained. The BET surface area of this catalyst was about 1 $m^2/g$.

<Ammonia Synthesis Reaction>

A reaction in which nitrogen gas ($N_2$) and hydrogen gas ($H_2$) react to produce ammonia gas ($NH_3$) was performed. The obtained catalyst in an amount of 0.2 g was charged into a glass tube, and the reaction was performed by a fixed bed flow reactor. The gas flows were set to $N_2$: 15 mL/min and $H_2$: 45 mL/min giving a total of 60 mL/min, and the reaction was performed at a pressure of atmospheric pressure and a reaction temperature of 400° C. The gas that had emerged from the flow reactor was bubbled in a 0.005 M aqueous sulfuric acid solution to dissolve the produced ammonia in the solution, and the produced ammonium ions were quantified by an ion chromatograph. The production rate of ammonia at 400° C. was 2,760 $\mu molg^{-1}h^{-1}$.

Reference Example 2

<Synthesis of $Ca(NH_2)_2/ZrO_2$ Supporting Ru>

$ZrO_2$ (SZ31164, Saint-Gobain NorPro) with a specific surface area of 100 $m^2/g$ was evacuated at 500° C. for 5 hours and was then put into a stainless pressure-resistant container within a glove box in an Ar atmosphere, and metal Ca was put thereinto so as to be 40 wt % as $Ca(NH_2)_2$. The sealed pressure-resistant container was taken out of the glove box, and ammonia gas was introduced thereto, while being cooled to about −50° C. The pressure-resistant container was agitated for a while, was heated at 100° C. for 2 hours, and was cooled to room temperature to remove the ammonia gas. The obtained powder ($Ca(NH_2)_2/ZrO_2$) was collected within the glove box in an Ar atmosphere. Next, the powder ($Ca(NH_2)_2/ZrO_2$) was physically mixed with $Ru_3(CO)_{12}$ so as to give a Ru support amount of 5 wt % relative to $Ca(NH_2)_2/ZrO_2$ and was encapsulated in vacuum quartz glass. The encapsulated sample was heated at 250° C. for 15 hours. With this procedure, a $Ca(NH_2)_2/ZrO_2$ catalyst supporting Ru metal was obtained. The BET surface area of this catalyst was 64 $m^2/g$.

<Ammonia Synthesis Reaction>

A reaction in which nitrogen gas ($N_2$) and hydrogen gas ($H_2$) react to produce ammonia gas ($NH_3$) was performed. The obtained catalyst in an amount of 0.2 g was charged into a glass tube, and the reaction was performed by a fixed bed flow reactor. The gas flows were set to $N_2$: 15 mL/min and $H_2$: 45 mL/min giving a total of 60 mL/min, and the reaction was performed at a pressure of atmospheric pressure and a reaction temperature of 340° C. The gas that had emerged from the flow reactor was bubbled in a 0.005 M aqueous sulfuric acid solution to dissolve the produced ammonia in the solution, and the produced ammonium ions were quantified by an ion chromatograph. The production rate of ammonia at 340° C. was 7,387 $\mu molg^{-1}h^{-1}$.

Reference Example 3

<Synthesis of $Ca(NH_2)_2/ZrO_2$ Supporting Ru>

$ZrO_2$ powder (manufactured by Saint-Gobain NorPro, Product No.: SZ 31164) in an amount of 0.67 g was put into a quartz glass container and was evacuated at 500° C. for 5 hours to perform dehydration treatment. The dehydrated $ZrO_2$ powder was put into a 30 cc stainless steel pressure-resistant container within a glove box in an Ar atmosphere, and 0.25 g of metal Ca powder (purity: 99.99%, manufactured by Aldrich, Product No.: 215147) was put thereinto so as to give 40 wt % of $Ca(NH_2)_2$ to be produced relative to a total amount together with $ZrO_2$.

The sealed pressure-resistant container was taken out of the glove box. The pressure-resistant container was immersed in ethanol, and ammonia gas was introduced thereto, while being cooled to about −50° C. Liquid ammonia was charged into the pressure-resistant container, and the pressure-resistant container was agitated at 1,000 rpm for 1 hour. The pressure-resistant container was immersed in an oil bath to perform a heating reaction at 100° C. and was agitated at 500 rpm for 2 hours. After the pressure-resistant container was cooled to room temperature, the residual ammonia gas was removed from the pressure-resistant container. $Ca(NH_2)_2/ZrO_2$ within the pressure-resistant container was collected within a glove box in an Ar atmosphere.

$Ca(NH_2)_2/ZrO_2$ powder in an amount of 0.30 g and $Ru_3(CO)_{12}$ powder (99%, manufactured by Aldrich, Product No.: 245011) in an amount of 0.035 g were mixed using an agate mortar so as to give a Ru support amount of 5 wt % relative to $Ru/Ca(NH_2)_2/ZrO_2$ catalyst, and the mixture was encapsulated in a vacuum Pyrex (registered trademark) tube. The sample put into the Pyrex tube was heated at 250° C. for 15 hours. With this procedure, 0.29 g of a catalyst in which the $Ca(NH_2)_2/ZrO_2$ powder supports Ru metal was obtained.

<Production of Ammonia Water>

A reaction in which nitrogen gas ($N_2$) and hydrogen gas ($H_2$) react to produce ammonia gas ($NH_3$) was performed. The obtained catalyst in an amount of 0.2 g was charged into a pressure-resistant tube, and the reaction was performed by a fixed bed flow reactor. The gas flows were set to $N_2$: 15 mL/min and $H_2$: 45 mL/min giving a total of 60 mL/min, and the reaction was performed at a pressure of 0.9 MPa and a reaction temperature of 340° C. The gas that had emerged from the fixed bed flow reactor was passed through water cooled at about 3° C. to dissolve the produced $NH_3$ in the water, and the produced ammonium ions ($NH_4^+$) were quantified by an ion chromatograph. The production rate of ammonia at 340° C. was 13,624 $\mu molg^{-1}h^{-1}$. After that, Aqueous Ammonia 1 (liquid amount: 200 g, $NH_4^+$ amount: 1.78 g) was obtained in about 43 hours.

Reference Example 4

<Production of Ammonia Water>

Using a catalyst similar to that of Reference Example 3, $NH_3$ produced by a method similar to that of Reference Example 3 was dissolved in water to obtain an aqueous ammonia (liquid amount: 200 g, $NH_4^+$ amount: 3.02 g) in about 92 hours.

<Concentrating Ammonia Water>

Concentration was performed using the obtained aqueous ammonia. The obtained aqueous ammonia (200 g) was put into a concentration side flask and was heated at 90° C. $NH_3$ gas that had volatilized was passed through 100 g of cooled receiver tank water to dissolve $NH_3$, and $NH_4^+$ in the receiver tank water was quantified by an ion chromatograph. Ar gas (50 mL/min) was passed through the concentration side flask to promote the volatilization of $NH_3$ gas. Based on this condition, Aqueous Ammonia 2 (liquid amount: 100 g, $NH_4^-$ amount: 1.89 g) was obtained in about 5 hours. The concentration rate was 1.29 ($NH_4^+$ concentration after concentration: 18.9 g/L, $NH_4^+$ concentration before concentration: 14.7 g/L).

Reference Example 5

<Production of Ammonia Water>

In Reference Example 3, the pressure condition was changed from 0.9 MPa to 0.1 MPa. Ammonia water was produced similarly to Reference Example 3 except the above matter. The production rate of ammonia at 340° C. was 6,059 $\mu molg^{-1}h^{-1}$. Aqueous Ammonia 3 (liquid amount: 100 g, $NH_4^+$ amount: 0.81 g) was obtained in about 49 hours.

Reference Example 6

<Production of Ammonium Sulfate>

In Reference Example 3, the reaction temperature was changed from 340° C. to 400° C., and besides, being passed through the water cooled at about 3° C. was changed to being passed through a 0.220 M aqueous sulfuric acid solution at room temperature. Ammonium sulfate was produced similarly to Reference Example 3 except the above matters. The production rate of ammonia at 400° C. was 16,029 $\mu molg^{-1}h^{-1}$. Ammonium Sulfate Solution 1 (liquid amount: 100 g, $NH_4^+$ amount: 0.92 g) was obtained in about 17 hours.

Reference Example 7

<Synthesis of C12A7e$^{21}$ Supporting Ru>

$CaCO_3$ (purity: 99.99%, manufactured by Kojundo Chemical Laboratory Co., Ltd., Product No.: CAH23PB) and $Al_2O_3$ (purity: 99.99%, manufactured by Kanto Chemical Co., Inc., Product No.: 01173), both in powder form, were mixed so as to give the molar ratio between Ca and Al of 11:7 and were heated in an alumina crucible at 1,300° C. for 6 hours. The obtained powder was inserted into a silica glass tube and was heated at 1,100° C. for 15 hours in a vacuum of $1\times10^{-4}$ Pa. The obtained powder in an amount of 3 g was inserted into a silica glass tube together with 0.18 g of metal Ca powder and was heated at 700° C. for 15 hours to make a metal Ca vapor atmosphere therewithin, and a $12CaO.7Al_2O_3$ electride (denoted by C12A7e$^{21}$) in powder form was obtained.

The C12A7e$^{21}$ powder in an amount of 1.00 g was dissolved in a hexane solvent, 0.04 g of $Ru_3(CO)_{12}$ was mixed therewith so as to give a Ru support amount of 2 wt % relative to a Ru/C12A7e$^{21}$ catalyst, and the solvent was evaporated to be dried and solidified. The obtained powder was heated in a vacuum at 100° C. for 4 hours to remove the residual solvent component, and a catalysis precursor was formed. The precursor was then subjected to heating treatment at 400° C. for 3 hours in a hydrogen gas (26.7 kPa) atmosphere to reduce $Ru_3(CO)_{12}$. A catalyst in which the C12A7e$^{21}$ powder supports Ru metal was obtained in an amount of 1.02 g.

<Production of Ammonia Water>

In Reference Example 3, the catalyst was changed from $Ca(NH_2)_2/ZrO_2$ supporting Ru to C12A7e$^{21}$ supporting Ru, the catalyst amount was changed from 0.2 g to 0.5 g, the pressure was changed to 0.5 MPa, and the reaction temperature was changed from 340° C. to 400° C. The ammonia water was produced similarly to Reference Example 3 except the above matters. The production rate of ammonia at 400° C. was 2,191 $\mu molg^{-1}h^{-1}$. Aqueous Ammonia 4 (liquid amount: 200 g, $NH_4^+$ amount: 2.04 g) was obtained in about 106 hours.

Reference Example 8

<Synthesis of $Ca_3N_2$ Supporting Ru>

$Ca_3N_2$ powder in an amount of 1.00 g (purity: 95%, manufactured by Aldrich, Product No.: 415103) was mixed with 0.04 g of $Ru_3(CO)_{12}$ powder using an agate mortar within a glove box in an Ar atmosphere so as to give a Ru support amount of 2 wt % relative to a Ru/$Ca_3N_2$ catalyst, and the mixture was encapsulated in a vacuum Pyrex tube. The sample put into the Pyrex tube was heated at 250° C. for 15 hours to obtain 1.02 g of a catalyst in which the $Ca_3N_2$ powder supports Ru metal.

<Molding Operation>

The obtained catalyst in an amount of 0.5 g was charged into a mold and was compressed to 10 MPa by a hydraulic pump, and a molded product was obtained using a molding apparatus (manufactured by JASCO Corporation, PT-10). The obtained molded product was roughly crushed with an agate mortar and was used as a molded catalyst (molded product) for the production of ammonia water.

<Production of Ammonia Water>

In Reference Example 3, the reaction temperature was changed from 340° C. to 400° C., the catalyst was changed from $Ca(NH_2)_2/ZrO_2$ supporting Ru to the molded product, and the catalyst amount was changed from 0.2 g to 0.4 g. Ammonia water was produced similarly to Reference Example 3 except the above matters. The production rate of ammonia at 400° C. was 2,142 $\mu molg^{-1}h^{-1}$. Aqueous Ammonia 5 (liquid amount: 200 g, $NH_4^+$ amount: 1.62 g) was obtained in about 101 hours.

Example 1

The ammonia gas synthesized in Reference Example 1 was dissolved in water to obtain ammonia water.

Ammonia gas was recovered from the obtained ammonia water using an ammonia stripping apparatus, and using the ammonia gas, *E. coli* MG1655 was cultured.

From a growing curve, the ammonia gas obtained was revealed to be able to be used for fermentation and culture production.

Example 2

The ammonia gas synthesized in Reference Example 2 was dissolved in water to obtain ammonia water.

Ammonia gas was recovered from the obtained ammonia water using an ammonia stripping apparatus, and using the ammonia gas, *E. coli* MG1655 was cultured.

From a growing curve, the ammonia gas obtained was revealed to be able to be used for fermentation and culture production.

Example 3

Using Aqueous Ammonia 1 produced in Reference Example 3 and *Escherichia coli*, the production culture of L-lysine was performed. The following media were used for the culture.

LB Agar Medium:
tryptone: 10 g/L, yeast extract: 5 g/L, NaCl: 10 g/L, agar: 15 g/L Lys Ammoniacal Liquor Medium:

glucose: 20 g/L, $NH_3$: 3.09 g/L (Aqueous Ammonia 1 was used), $MgSO_4.7H_2O$: 1 g/L, $KH_2PO_4$: 1 g/L, yeast extract: 2 g/L, $FeSO_4.7H_2O$: 0.01 g/L, $MnSO_4.5H_2O$: 0.008 g/L, adjusted to have a pH of 7.0 using $H_2SO_4$ Lys-producing bacteria WC196ΔcadAΔldc/pCABD2 were cultured in the LB agar medium with streptomycin added so as to have a final concentration of 80 mg/L at 37° C. for an entire day and night. All the bacteria on the plate with a diameter of 90 mm were scraped together from the LB agar medium after culture and were suspended in a 3 mL of a physiological saline solution to prepare a bacteria solution.

The bacteria solution was planted to a thick test tube charged with 5 mL of the Lys ammoniacal liquor medium to which streptomycin had been added so as to have a final concentration of 80 mg/L and calcium carbonate dry-sterilized in advance had been added so as to have a final concentration of 30 g/L so as to have an absorbance at a wavelength of 620 nm (O.D. 620 nm) of 0.126, and shake culture was performed at 37° C. and 120 rpm for 24 hours.

Example 4

In Example 3, Aqueous Ammonia 1 in the Lys ammoniacal liquor medium was changed to Aqueous Ammonia 2 produced in Reference Example 4. The production culture of L-lysine was performed similarly to Example 3 except the above matter.

Example 5

In Example 3, Aqueous Ammonia 1 in the Lys ammoniacal liquor medium was changed to Aqueous Ammonia 3 produced in Reference Example 5. The production culture of L-lysine was performed similarly to Example 3 except the above matter.

Example 6

In Example 3, the Lys ammoniacal liquor medium was changed to the following Lys ammonium sulfate medium. The production culture of L-lysine was performed similarly to Example 3 except the above matter.

Lys Ammonium Sulfate Medium:

glucose: 20 g/L, $(NH_4)_2SO_4$: 12 g/L (Ammonium Sulfate Solution 1 produced in Reference Example 6 was used), $MgSO_4.7H_2O$: 1 g/L, $KH_2PO_4$: 1 g/L, yeast extract: 2 g/L, $FeSO_4.7H_2O$: 0.01 g/L, $MnSO_4.5H_2O$: 0.008 g/L, adjusted to have a pH of 7.0 using KOH.

Example 7

In Example 3, Aqueous Ammonia 1 in the Lys ammoniacal liquor medium was changed to Aqueous Ammonia 4 produced in Reference Example 7. The production culture of L-lysine was performed similarly to Example 3 except the above matter.

Example 8

In Example 3, Aqueous Ammonia 1 in the Lys ammoniacal liquor medium was changed to Aqueous Ammonia 5 produced in Reference Example 8. The production culture of L-lysine was performed similarly to Example 3 except the above matter.

Comparative Example 1

In Example 3, Aqueous Ammonia 1 in the Lys ammoniacal liquor medium was changed to a commercially available aqueous ammonia (manufactured by Junsei Chemical Co., Ltd., Product No.: 13370-0301). The production culture of L-lysine was performed similarly to Example 3 except the above matter.

Comparative Example 2

In Example 6, Ammonium Sulfate Solution 1 in the Lys ammonium sulfate medium was changed to a commercially available ammonium sulfate solution (manufactured by Junsei Chemical Co., Ltd., Product No.: 83110-0367). The production culture of L-lysine was performed similarly to Example 6 except the above matter.

TABLE 1

| | Nitrogen source | O.D. 620 nm (xl) | Production amount of L-lysine (g/L) | Yield (%) |
|---|---|---|---|---|
| Example 3 | Aquaous Ammonia 1 | 9.78 ± 1.24 | 8.3 ± 0.1 | 38.1 ± 0.3 |
| Example 4 | Aquaous Ammonia 2 | 8.38 ± 0.13 | 7.7 ± 0.4 | 36.8 ± 1.8 |
| Example 5 | Aquaous Ammonia 3 | 8.81 ± 0.11 | 8.6 ± 0.0 | 39.0 ± 0.2 |
| Example 6 | Ammonium u Sulfate Solution 1 | 9.84 ± 0.13 | 8.4 ± 0.0 | 39.4 ± 0.2 |
| Example 7 | Aqueous Ammonia 4 | 8.43 ± 0.06 | 8.3 ± 0.1 | 39.1 ± 0.5 |
| Example 8 | Aqueous Ammonia 5 | 8.91 ± 1.08 | 8.3 ± 0.1 | 39.6 ± 0.5 |
| Comparative Example 1 | Ammonia water (commercially available product) | 8.45 ± 0.13 | 8.4 ± 0.1 | 39.5 ± 0.3 |
| Comparative Example 2 | Ammonium sulfate (commercially available product) | 10.22 ± 0.06 | 8.7 ± 0.1 | 40.2 ± 0.3 |

The culture results are listed in the above table. Also when Aqueous Ammonia 1 to 5 and Ammonium Sulfate Solution 1 prepared in any condition of Reference Examples 3 to 8 were used, bacterial growth and the production of L-lysine substantially equal to those of the examples cultured using the commercially available aqueous ammonia (Comparative Example 1) and the commercially available ammonium sulfate (Comparative Example 2) were revealed, showing that the ammonia gas can be used for fermentation and culture production.

Example 9

Using Aqueous Ammonia 1 produced in Reference Example 3 and *Corynebacterium glutamicum*, the production culture of L-glutamic acid was performed. The following media were used for the culture.

CM-Ace Agar Medium:

glucose: 2.5 g/L, fructose: 2.5 g/L, sodium gluconate: 4 g/L, sodium succinate.6H$_2$O: 2 g/L, peptone: 10 g/L, yeast extract: 10 g/L, KH$_2$PO$_4$: 1 g/L, MgSO$_4$.7H$_2$O: 0.4 g/L, FeSO$_4$.7H$_2$O: 0.01 g/L, MnSO$_4$.5H$_2$O: 0.01 g/L, urea: 4 g/L, bean filtrate (soybean hydrolysate): 1.2 g/L (T-N), biotin: 1 mg/L, vitamin B1: 5 mg/L, adjusted to have a pH of 7.5 using KOH.

Glu Ammoniacal Liquor Medium:

glucose: 40 g/L, NH$_3$: 3.86 g/L (Aqueous Ammonia 1 was used), KH$_2$PO$_4$: 1 g/L, MgSO$_4$.7H$_2$O: 0.4 g/L, FeSO$_4$.7H$_2$O: 0.01 g/L, MnSO$_4$.5H$_2$O: 0.01 g/L, vitamin B1: 200 μg/L, biotin: 300 μg/L, bean filtrate: 0.48 g/L (T-N), K$_2$SO$_4$: 19.78 g/L, adjusted to have a pH of 8.0 using H$_2$SO$_4$ Glu producing bacteria 2256ΔldhAΔsucAyggB* of *Corynebacterium glutamicum* were cultured in the CM-Ace agar medium at 31.5° C. for an entire day and night. The bacteria corresponding to 1/24 plate were scraped from the agar medium after culture and were planted to a thick test tube charged with 5 mL of the Glu ammoniacal liquor medium to which calcium carbonate dry-sterilized in advance had been added so as to have a final concentration of 30 g/L, and shake culture was performed at 31.5° C. and 120 rpm for 24 hours.

Example 10

In Example 9, Aqueous Ammonia 1 in the Glu ammoniacal liquor medium was changed to Aqueous Ammonia 2 produced in Reference Example 4. The production culture of L-glutamic acid was performed similarly to Example 9 except the above matter.

Example 11

In Example 9, Aqueous Ammonia 1 in the Glu ammoniacal liquor medium was changed to Aqueous Ammonia 3 produced in Reference Example 5. The production culture of L-glutamic acid was performed similarly to Example 9 except the above matter.

Example 12

In Example 9, the Glu ammoniacal liquor medium was changed to the following Glu ammonium sulfate medium. The production culture of L-glutamic acid was performed similarly to Example 9 except the above matter.

Glu Ammonium Sulfate Medium:

glucose: 40 g/L, (NH$_4$)$_2$SO$_4$: 15 g/L (Ammonium Sulfate Solution 1 produced in Reference Example 6 was used), KH$_2$PO$_4$: 1 g/L, MgSO$_4$.7H$_2$O: 0.4 g/L, FeSO$_4$.7H$_2$O: 0.01 g/L, MnSO$_4$.5H$_2$O: 0.01 g/L, vitamin B1: 200 μg/L, biotin: 300 μg/L, bean filtrate: 0.48 g/L (T-N), adjusted to have a pH of 8.0 using KOH.

Example 13

In Example 9, Aqueous Ammonia 1 in the Glu ammoniacal liquor medium was changed to Aqueous Ammonia 4 produced in Reference Example 7. The production culture of L-glutamic acid was performed similarly to Example 9 except the above matter.

Example 14

In Example 9, Aqueous Ammonia 1 in the Glu ammoniacal liquor medium was changed to Aqueous Ammonia 5 produced in Reference Example 8. The production culture of L-glutamic acid was performed similarly to Example 9 except the above matter.

Comparative Example 3

In Example 9, Aqueous Ammonia 1 in the Glu ammoniacal liquor medium was changed to a commercially available aqueous ammonia (manufactured by Junsei Chemical Co., Ltd., Product No.: 13370-0301). The production culture of L-glutamic acid was performed similarly to Example 9 except the above matter.

Comparative Example 4

In Example 12, Ammonium Sulfate Solution 1 in the Glu ammonium sulfate medium was changed to a commercially available ammonium sulfate solution (manufactured by Junsei Chemical Co., Ltd., Product No.: 83110-0367). The production culture of L-glutamic acid was performed similarly to Example 12 except the above matter.

TABLE 2

| | Nitrogen source | O.D. 620 nm (xl) | Production amount of L-glutamic acid (g/L) | Yield (%) |
|---|---|---|---|---|
| Example 9 | Aqueous Ammonia 1 | 31.20 ± 0.50 | 20.5 ± 0.4 | 49.5 ± 0.9 |
| Example 10 | Aqueous Ammonia 2 | 32.15 ± 0.43 | 21.8 ± 0.4 | 51.7 ± 0.9 |
| Example 11 | Aqueous Ammonia 3 | 30.52 ± 0.06 | 19.9 ± 0.2 | 51.2 ± 0.6 |
| Example 12 | Ammonium u Sulfate Solution 1 | 26.83 ± 0.98 | 20.1 ± 0.1 | 48.4 ± 0.3 |
| Example 13 | Aqueous Ammonia 4 | 32.37 ± 0.24 | 20.4 ± 0.2 | 50.2 ± 0.5 |
| Example 14 | Aqueous Ammonia 5 | 31.86 ± 0.68 | 20.2 ± 0.3 | 50.0 ± 0.7 |
| Comparative Example 3 | Ammonia water (commercially available product) | 33.59 ± 0.56 | 20.8 ± 0.2 | 48.6 ± 0.5 |
| Comparative Example 4 | Ammonium u sulfate (commericially available product) | 29.65 ± 0.68 | 21.8 ± 0.0 | 51.2 ± 0.0 |

The culture results are listed in the above table. Also when Aqueous Ammonia 1 to 5 and Ammonium Sulfate Solution 1 prepared in any condition of Reference Examples 3 to 8 were used, bacterial growth and the production of L-glutamic acid substantially equal to those of the examples cultured using the commercially available aqueous ammonia (Comparative Example 3) and the commercially available ammonium sulfate (Comparative Example 4) were revealed, showing that the ammonia gas can be used for fermentation and culture production.

REFERENCE SIGNS LIST

1 Hydrogen source gas
2 Air
3 Source gas containing hydrogen and nitrogen
4 Ammonia-containing gas
5, 9, 12, 15 Recovered gas
6 Concentrated ammonia
7 Water
8 Ammonia water
10 Carbon dioxide
11 Urea
12 Water removed by ammonia stripping apparatus
13 Air
14 Fermented and cultured product
101 Hydrogen/nitrogen production apparatus
102 Ammonia synthesis apparatus
103 Ammonia concentration apparatus
104, 105 Gas separation membrane
106 Cooler
107 Dehydrator
108 Drier
201 Product production apparatus (dissolving tank)
202 Product production apparatus (urea production apparatus)
203 Product production apparatus (fermentation and culture tank)
204 Premixer
205 Ammonia stripping apparatus
1000, 1001, 1002 Production system for ammonia water
2000, 2001, 2002 Production system for urea
3000, 3001, 3002, 3003 Production system for fermented and cultured product

The invention claimed is:

1. A production system useful for reacting a source gas and a metal catalyst to produce a product selected from the group consisting of a nitrogen-containing product and a fermented and cultured product, the production system comprising:
A) an ammonia synthesis apparatus and a support, the ammonia synthesis apparatus capable of reacting a source gas comprising hydrogen and nitrogen in the presence of a metal catalyst and said support, wherein said support is selected from the group consisting of:
   i) a conductive mayenite compound;
   ii) a two-dimensional electride compound or a precursor thereof;
   iii) a complex formed of a support base comprising:
      a metal oxide selected from the group consisting of $ZrO_2$, $TiO_2$, $CeO_2$, MgO, and combinations thereof, and
      a metal amide represented by a formula $M(NH_2)_x$, wherein M is selected from the group consisting of Li, Na, K, Be, Mg, Ca, Sr, Ba, Eu, and combinations thereof, and x represents a valence number of M; and
   iv) combinations thereof;
wherein an ammonia-containing gas is synthesized; and
B) a production apparatus that is capable of producing said product using ammonia originating from said ammonia-containing gas;
wherein the production system comprises an ammonia concentration apparatus selected from the group consisting of a pressurized cooling apparatus, a gas separation membrane apparatus, and a pressure swing adsorption (PSA) apparatus;
wherein the production system is capable of
   producing ammonia water using ammonia originating from said ammonia-containing gas,
   recovering ammonia gas from said ammonia water, and
   producing a fermented and cultured product using the recovered ammonia gas.

2. The production system according to claim 1, wherein said source gas is reacted under conditions comprising a reaction temperature of 530° C. or lower and a reaction pressure of 30 MPa or lower.

3. The production system according to claim 1, further comprising a recycle apparatus that recovers unreacted hydrogen and nitrogen following said reaction in the ammonia synthesis apparatus, and returns said unreacted hydrogen and nitrogen to be reacted again in the ammonia synthesis apparatus.

4. The production system according to claim 3, wherein the recycle apparatus comprises a dehydrator and/or a drier capable of removing water from said unreacted hydrogen and nitrogen.

5. The production system according to claim 1, wherein the nitrogen-containing product is selected from the group consisting of ammonia water, ammonium salts, urea, nitric acid, and nitrates.

6. The production system according to claim 1, wherein the fermented and cultured product is selected from the group consisting of amino acids, organic acids, polysaccharides, proteins, antibiotics, alcohols, and microbial cells.

* * * * *

UNITED STATES PATENT AND TRADEMARK OFFICE
CERTIFICATE OF CORRECTION

PATENT NO. : 10,941,427 B2
APPLICATION NO. : 15/675068
DATED : March 9, 2021
INVENTOR(S) : Mitsuhiro Kishino et al.

It is certified that error appears in the above-identified patent and that said Letters Patent is hereby corrected as shown below:

On the Title Page

Item (63), should be amended as follows:
Continuation of application No. PCT/JP2016/054610, filed on February 17, 2016.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*